United States Patent
Inoue et al.

(10) Patent No.: US 10,115,912 B2
(45) Date of Patent: Oct. 30, 2018

(54) ORGANOMETALLIC COMPLEX, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Hideko Inoue, Kanagawa (JP); Miki Kanamoto, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 93 days.

(21) Appl. No.: 15/137,460

(22) Filed: Apr. 25, 2016

(65) Prior Publication Data
US 2016/0322590 A1 Nov. 3, 2016

(30) Foreign Application Priority Data
Apr. 28, 2015 (JP) ................. 2015-091000

(51) Int. Cl.
| H01L 51/00 | (2006.01) |
| H01L 27/32 | (2006.01) |
| C07F 15/00 | (2006.01) |
| C09K 11/06 | (2006.01) |

(52) U.S. Cl.
CPC ...... *H01L 51/0087* (2013.01); *C07F 15/0086* (2013.01); *C09K 11/06* (2013.01); *H01L 27/3248* (2013.01); *H01L 27/3262* (2013.01); *C09K 2211/1007* (2013.01); *C09K 2211/1022* (2013.01); *C09K 2211/1029* (2013.01); *C09K 2211/1037* (2013.01); *C09K 2211/1044* (2013.01); *C09K 2211/1092* (2013.01); *C09K 2211/185* (2013.01)

(58) Field of Classification Search
CPC .................................................. C07F 15/0086
See application file for complete search history.

(56) References Cited

U.S. PATENT DOCUMENTS

| 6,097,147 | A | 8/2000 | Baldo et al. |
| 7,041,390 | B2 | 5/2006 | Seo et al. |
| 7,176,307 | B2 | 2/2007 | Seo et al. |
| 8,816,080 | B2 | 8/2014 | Li et al. |
| 8,927,713 | B2 | 1/2015 | Li et al. |
| 9,238,668 | B2 | 1/2016 | Li et al. |
| 2002/0034656 | A1 | 3/2002 | Thompson et al. |
| 2002/0064681 | A1 | 5/2002 | Takiguchi et al. |
| 2003/0017361 | A1 | 1/2003 | Thompson et al. |
| 2006/0106211 | A1 | 5/2006 | Seo et al. |
| 2012/0215001 | A1* | 8/2012 | Li ............ C07F 15/0086 546/4 |
| 2015/0287938 | A1 | 10/2015 | Li et al. |

FOREIGN PATENT DOCUMENTS

| JP | 2003-342284 A | 12/2003 |
| WO | WO 2004/081019 A1 | 9/2004 |
| WO | WO 2012/112853 A1 | 8/2012 |
| WO | WO 2012/162488 A1 | 11/2012 |

OTHER PUBLICATIONS

Thompson, M.E. et al., "Phosphorescent Materials and Devices," Proceedings of the 10th International Workshop on Inorganic and Organic Electroluminescence (EL'00), Dec. 4, 2000, pp. 35-38.
Baldo, M.A. et al., "High-Efficiency Fluorescent Organic Light-Emitting Devices Using a Phosphorescent Sensitizer," Nature, Feb. 17, 2000, vol. 403, pp. 750-753.
Tsutsui, T. et al., "High Quantum Efficiency in Organic Light-Emitting Devices With Iridium-Complex as a Triplet Emissive Center," Japanese Journal of Applied Physics, Dec. 15, 1999, vol. 38, No. 12B, pp. L1502-L1504.
O'Brien, D.F. et al., "Improved Energy Transfer in Electrophosphorescent Devices," Applied Physics Letters, Jan. 18, 1999, vol. 74, No. 3, pp. 442-444.
Inoue, H. et al., "A Reaction of Singlet Oxygen With an Unsaturated Organic Molecule, 6.1.4, Quencher and Photosensitizer," Basic Chemistry Course Photochemistry I , Sep. 30, 1999, pp. 106-110, Maruzen.
Tsutsui, T., "Mechanism of Organic El Element and Luminous Efficiency," Textbook of the 3rd Seminar at Division of Organic Molecular Electronics and Bioelectronics, 1993, pp. 31-37, Division of Molecular Electronics and Bioelectronics The Japan Society of Applied Physics.

* cited by examiner

Primary Examiner — Kuo Liang Peng
(74) Attorney, Agent, or Firm — Husch Blackwell LLP

(57) ABSTRACT

An object is to provide a novel organometallic complex. Another object is to provide an organometallic complex that can exhibit yellow to blue phosphorescence. A platinum complex with a tetracoordinate ligand including a phenothiazine skeleton or a phenoxazine skeleton is provided. In the ligand, nitrogen at the 10-position and carbon at the 2-position of the phenothiazine skeleton or the phenoxazine skeleton have a pyridyl group and a phenoxy group, respectively. A five-membered heteroaromatic residue is present at the 3-position of the phenoxy group. The five-membered heteroaromatic residue has two or three nitrogen atoms in its skeleton. Carbon at the 1-position of the phenothiazine skeleton or the phenoxazine skeleton and carbon at the 2-position of the phenoxy group are bonded to platinum, and nitrogen of the pyridyl group and nitrogen or carbene carbon of the five-membered heteroaromatic residue are coordinated to platinum.

8 Claims, 19 Drawing Sheets

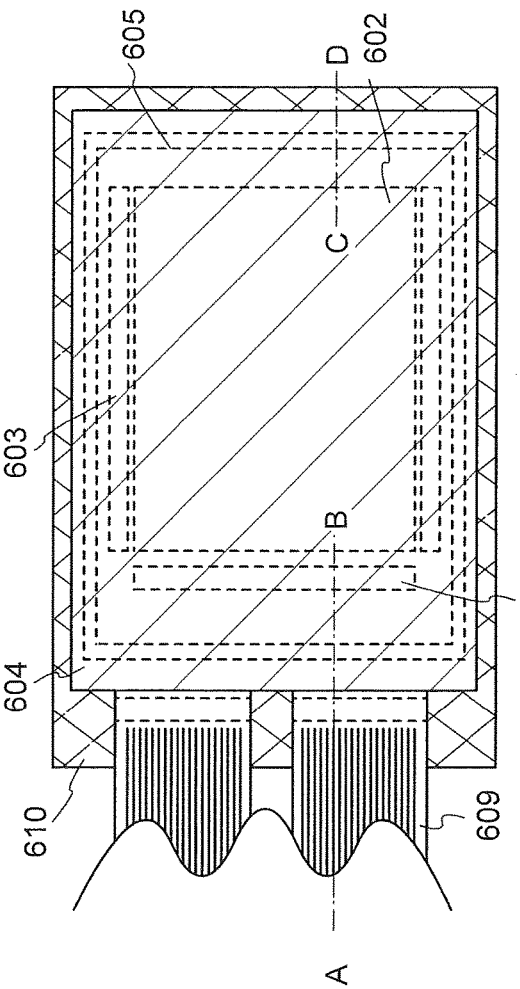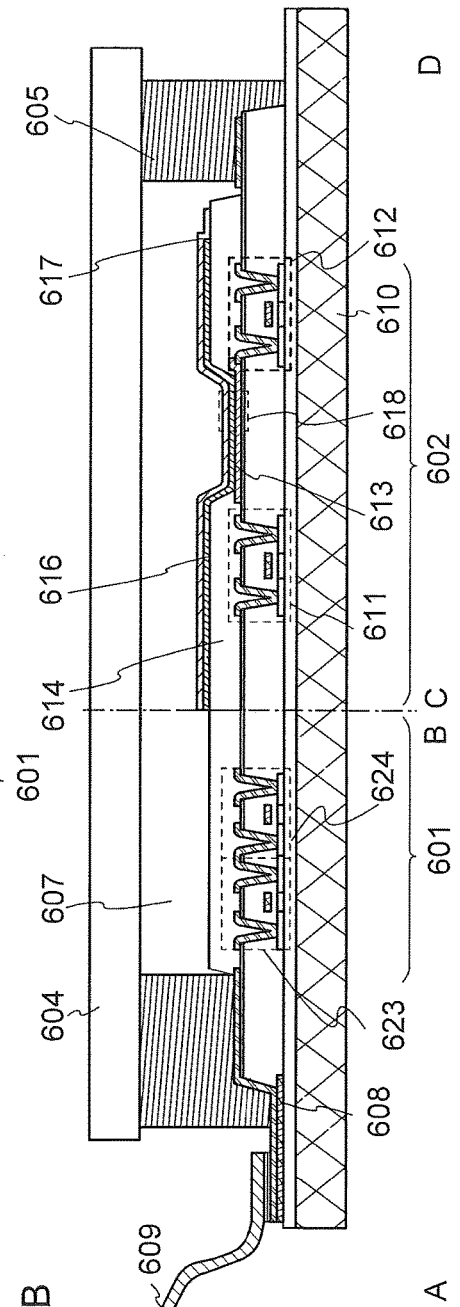
FIG. 2A
FIG. 2B

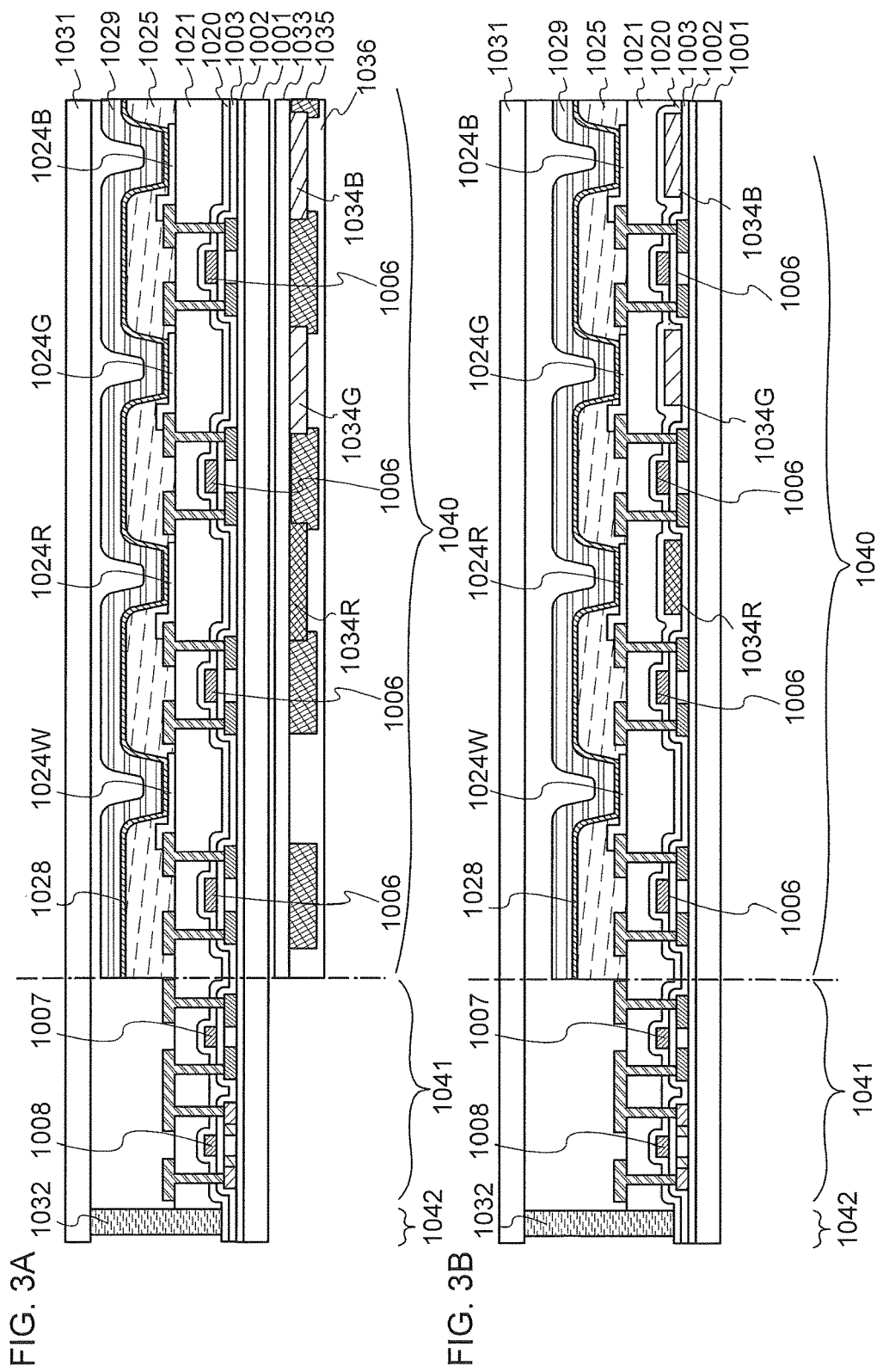

FIG. 7A
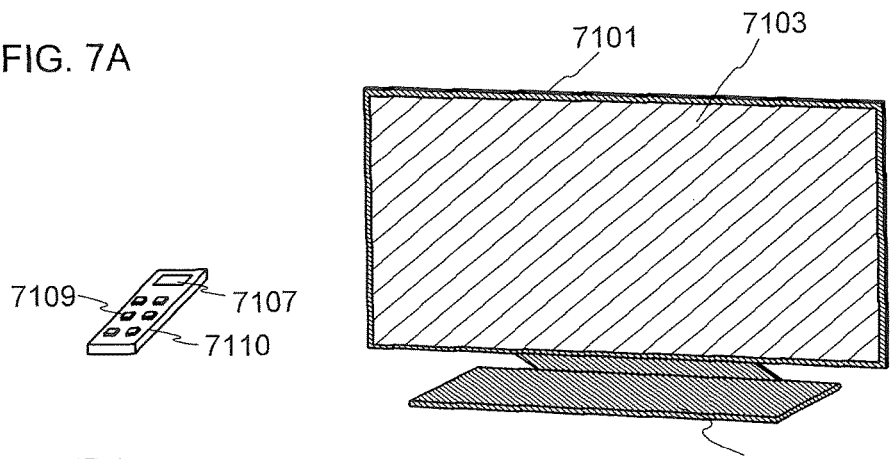
FIG. 7B1
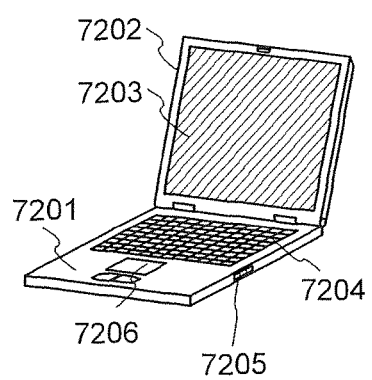
FIG. 7B2
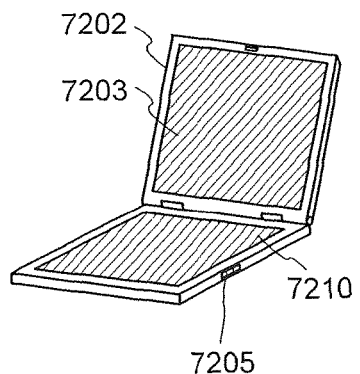
FIG. 7C
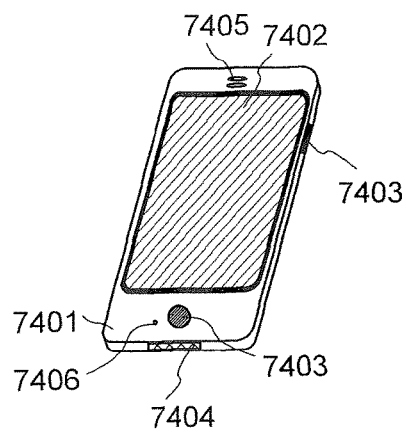
FIG. 7D
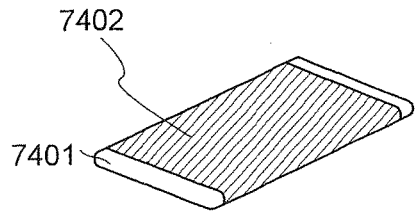

ORGANOMETALLIC COMPLEX, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

One embodiment of the present invention relates to an organometallic complex, and a light-emitting element, a display module, a lighting module, a display device, a light-emitting device, an electronic device, and a lighting device each including the organometallic complex. Note that one embodiment of the present invention is not limited to the above technical field. The technical field of one embodiment of the invention disclosed in this specification and the like relates to an object, a method, or a manufacturing method. In addition, one embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting device, a lighting device, a power storage device, a memory device, a method for driving any of them, and a method for manufacturing any of them.

2. Description of the Related Art

As next generation lighting devices or display devices, display devices using light-emitting elements (organic EL elements) in which organic compounds or organometallic complexes are used as light-emitting substances have been developed and reported because of their potential for thinness, lightness, high-speed response to input signals, low power consumption, and the like.

In an organic EL element, voltage application between electrodes, between which a light-emitting layer is interposed, causes recombination of electrons and holes injected from the electrodes, which brings a light-emitting substance into an excited state, and the return from the excited state to the ground state is accompanied by light emission. Since the spectrum of light emitted from a light-emitting substance depends on the light-emitting substance, use of different types of light-emitting substances makes it possible to obtain light-emitting elements which exhibit various colors.

Although displays or lighting devices including light-emitting elements can be suitably used for a variety of electronic devices as described above, their performance has plenty of room to improve. Specifically, there have not been many kinds of materials that emit green to blue phosphorescence, and further improvement of their characteristics has been demanded.

Patent Document 1 discloses an iridium complex with a ligand including a phenothiazine skeleton.

REFERENCE

Patent Document

[Patent Document 1] PCT International Publication No. 2004/081019

SUMMARY OF THE INVENTION

An object of one embodiment of the present invention is to provide a novel organometallic complex. Another object is to provide an organometallic complex that can exhibit yellow to blue phosphorescence.

An object of another embodiment of the present invention is to provide a novel light-emitting element. Another object is to provide a light-emitting element with high emission efficiency. Another object is to provide a display module, a lighting module, a light-emitting device, a display device, an electronic device, and a lighting device each having low power consumption.

It is only necessary that at least one of the above objects be achieved in one embodiment of the present invention. Note that the description of these objects does not preclude the existence of other objects. One embodiment of the present invention does not necessarily have all these objects. Other objects will be apparent from and can be derived from the description of the specification, the drawings, the claims, and the like.

An organometallic complex of one embodiment of the present invention can be represented by the following general formula (G1).

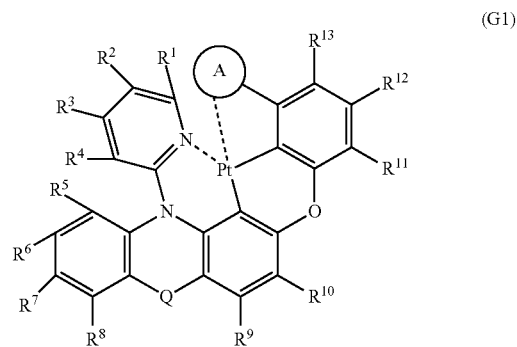

(G1)

In the above general formula (G1), each of $R^1$ to $R^{13}$ independently represents any of hydrogen, a substituted or unsubstituted alkyl group having 1 to 6 carbon atoms, and a substituted or unsubstituted phenyl group, A represents a five-membered heteroaromatic skeleton including two or three nitrogen atoms, and Q represents a sulfur atom or an oxygen atom.

The organometallic complex of one embodiment of the present invention can also be represented by the following general formula (G2).

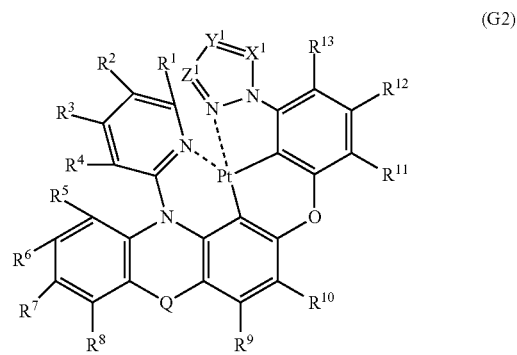

(G2)

In the above general formula (G2), each of $R^1$ to $R^{13}$ independently represents any of hydrogen, a substituted or unsubstituted alkyl group having 1 to 6 carbon atoms, and a substituted or unsubstituted phenyl group, and each of $X^1$, $Y^1$, and $Z^1$ independently represents a nitrogen atom or a carbon atom. Note that none or one of $X^1$, $Y^1$, and $Z^1$ represents a nitrogen atom. In addition, Q represents a sulfur atom or an oxygen atom.

Two or three of $X^1$, $Y^1$, and $Z^1$ each represent a carbon atom, and the carbon atom may have a substituent. In such a case, as the substituent, a substituted or unsubstituted alkyl group having 1 to 6 carbon atoms or a substituted or unsubstituted phenyl group can be used.

The organometallic complex of one embodiment of the present invention can also be represented by the following general formula (G3).

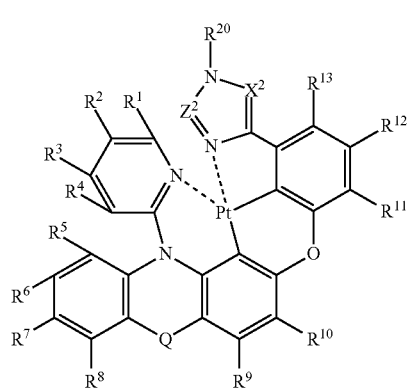

(G3)

In the above general formula (G3), each of $R^1$ to $R^{13}$ and $R^{20}$ independently represents any of hydrogen, a substituted or unsubstituted alkyl group having 1 to 6 carbon atoms, and a substituted or unsubstituted phenyl group, and each of $X^2$ and $Z^2$ independently represents a nitrogen atom or a carbon atom. When one of $X^2$ and $Z^2$ represents a nitrogen atom, the other thereof represents a carbon atom. In addition, Q represents a sulfur atom or an oxygen atom.

When one or both of $X^2$ and $Z^2$ represent a carbon atom, the carbon atom may have a substituent. In such a case, as the substituent, a substituted or unsubstituted alkyl group having 1 to 6 carbon atoms or a substituted or unsubstituted phenyl group can be used.

The organometallic complex of one embodiment of the present invention can also be represented by the following general formula (G4).

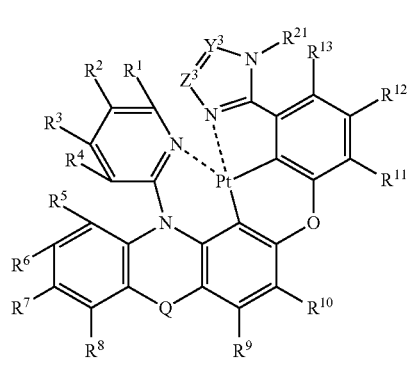

(G4)

In the above general formula (G4), each of $R^1$ to $R^{13}$ and $R^{21}$ independently represents any of hydrogen, a substituted or unsubstituted alkyl group having 1 to 6 carbon atoms, and a substituted or unsubstituted phenyl group, and each of $Y^3$ and $Z^3$ independently represents a nitrogen atom or a carbon atom. When one of $Y^3$ and $Z^3$ represents a nitrogen atom, the other thereof represents a carbon atom. In addition, Q represents a sulfur atom or an oxygen atom.

When one or both of $Y^3$ and $Z^3$ represent a carbon atom, the carbon atom may have a substituent. In such a case, as the substituent, a substituted or unsubstituted alkyl group having 1 to 6 carbon atoms or a substituted or unsubstituted phenyl group can be used.

The organometallic complex of one embodiment of the present invention can also be represented by the following general formula (G5).

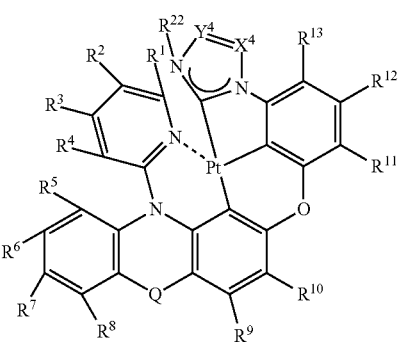

(G5)

In the above general formula (G5), each of $R^1$ to $R^{13}$ and $R^{22}$ independently represents any of hydrogen, a substituted or unsubstituted alkyl group having 1 to 6 carbon atoms, and a substituted or unsubstituted phenyl group, and each of $X^4$ and $Y^4$ independently represents a nitrogen atom or a carbon atom. When one of $X^4$ and $Y^4$ represents a nitrogen atom, the other thereof represents a carbon atom. In addition, Q represents a sulfur atom or an oxygen atom.

When one or both of $X^4$ and $Y^4$ represent a carbon atom, the carbon atom may have a substituent. In such a case, as the substituent, a substituted or unsubstituted alkyl group having 1 to 6 carbon atoms or a substituted or unsubstituted phenyl group can be used.

The organometallic complex of one embodiment of the present invention can also be represented by the following general formula (G6).

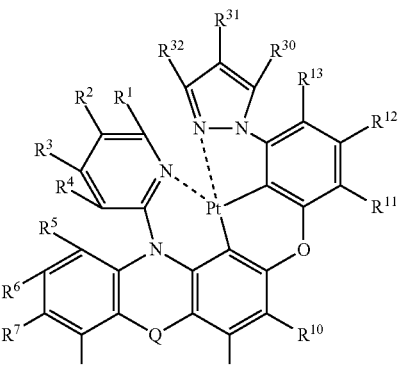

(G6)

In the above general formula (G6), each of $R^1$ to $R^{13}$ and $R^{30}$ to $R^{32}$ independently represents any of hydrogen, a substituted or unsubstituted alkyl group having 1 to 6 carbon atoms, and a substituted or unsubstituted phenyl group, and Q represents a sulfur atom or an oxygen atom.

Another embodiment of the present invention is an organometallic complex which has the above structure and in which each of $R^{30}$ and $R^{32}$ represents a substituted or unsubstituted alkyl group.

Another embodiment of the present invention is an organometallic complex which has any of the above structures and in which $R^{31}$ represents a substituted or unsubstituted alkyl group or a substituted or unsubstituted phenyl group.

Another embodiment of the present invention is an organometallic complex which has any of the above structures and in which $R^3$ represents a substituted or unsubstituted alkyl group or a substituted or unsubstituted phenyl group.

Another embodiment of the present invention is an organometallic complex which has any of the above structures and in which one or both of $R^3$ and $R^{31}$ represent a t-butyl group or a phenyl group.

Another embodiment of the present invention is a light-emitting element including any one of the above organometallic complexes.

Another embodiment of the present invention is a light-emitting device including the above light-emitting element, and a transistor or a substrate.

Another embodiment of the present invention is an electronic device including the above light-emitting device, and a sensor, an operation button, a speaker, or a microphone.

Another embodiment of the present invention is a lighting device including the above light-emitting device and a housing.

Note that the light-emitting device in this specification includes an image display device using a light-emitting element. The light-emitting device may be included in a module in which a light-emitting element is provided with a connector such as an anisotropic conductive film or a tape carrier package (TCP), a module in which a printed wiring board is provided at the end of a TCP, and a module in which an integrated circuit (IC) is directly mounted on a light-emitting element by a chip on glass (COG) method. The light-emitting device may be included in lighting equipment.

One embodiment of the present invention makes it possible to provide a novel organometallic complex. One embodiment of the present invention makes it possible to provide an organometallic complex exhibiting yellow to blue phosphorescence.

Another embodiment of the present invention makes it possible to provide a novel light-emitting element. Another embodiment of the present invention makes it possible to provide a display module, a lighting module, a light-emitting device, a display device, an electronic device, and a lighting device each having low power consumption.

It is only necessary that at least one of the above effects be achieved in one embodiment of the present invention. Note that the description of these effects does not preclude the existence of other effects. One embodiment of the present invention does not necessarily achieve all the effects listed above. Other effects will be apparent from and can be derived from the description of the specification, the drawings, the claims, and the like.

BRIEF DESCRIPTION OF THE DRAWINGS

FIGS. 2A and 2B are conceptual diagrams of an active matrix light-emitting device.

FIGS. 3A and 3B are conceptual diagrams of active matrix light-emitting devices.

FIGS. 7A, 7B1, 7B2, 7C, and 7D illustrate electronic devices.

DETAILED DESCRIPTION OF THE INVENTION

Figure 1A:
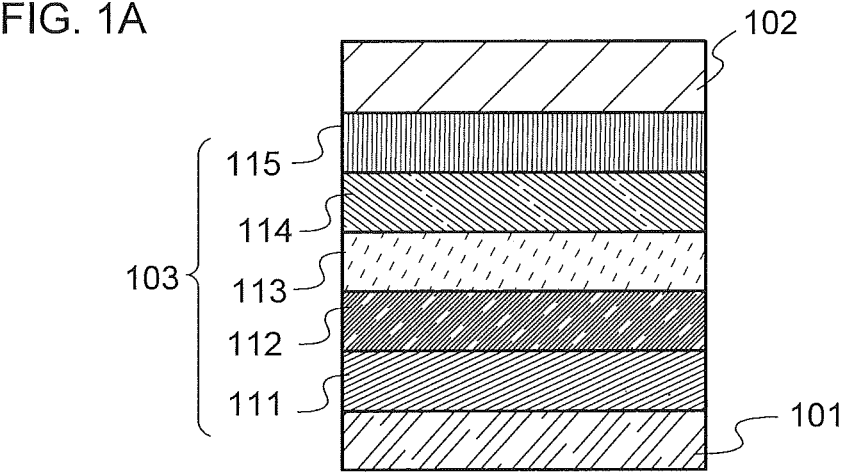
FIGS. 1A to 1C are conceptual diagrams of light-emitting elements.

Embodiments of the present invention will be explained in detail below with reference to the drawings. Note that the present invention is not limited to the description below, and it is easily understood by those skilled in the art that modes and details can be modified in various ways without departing from the spirit and scope of the present invention. Accordingly, the present invention should not be interpreted as being limited to the content of the embodiments below.

One embodiment of the present invention is a platinum complex with a tetracoordinate ligand including a phenothiazine skeleton or a phenoxazine skeleton. In the ligand, nitrogen at the 10-position and carbon at the 2-position of the phenothiazine skeleton or the phenoxazine skeleton have a pyridyl group and a phenoxy group, respectively. A five-membered heteroaromatic residue is present at the 3-position of the phenoxy group. The five-membered heteroaromatic residue has two or three nitrogen atoms in its skeleton. In addition, carbon at the 1-position of the phenothiazine skeleton or the phenoxazine skeleton and carbon at the 2-position of the phenoxy group are bonded to platinum, and nitrogen of the pyridyl group and nitrogen or carbene carbon of the five-membered heteroaromatic residue are coordinated to platinum.

An organometallic complex having such a structure is a novel organometallic complex and can emit yellow to blue phosphorescence.

The organometallic complex can also be represented by the following general formula (G1).

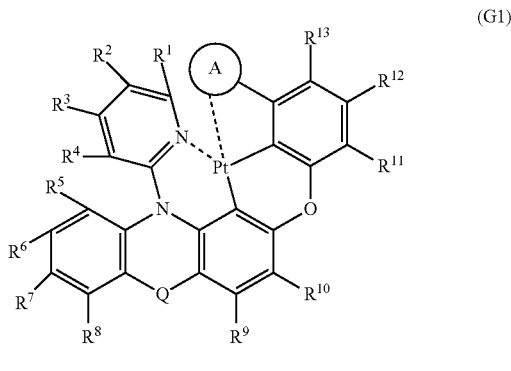

(G1)

In the above general formula (G1), each of $R^1$ to $R^{13}$ independently represents any of hydrogen, a substituted or unsubstituted alkyl group having 1 to 6 carbon atoms, and a substituted or unsubstituted phenyl group, A represents a five-membered heteroaromatic skeleton including two or three nitrogen atoms, and Q represents a sulfur atom or an oxygen atom.

Specific examples of the five-membered heteroaromatic skeleton including two or three nitrogen atoms are a pyrazolyl group, an imidazolyl group, a 1,2,3-triazolyl group, a 1,2,4-triazolyl group, a nitrogen-containing heterocyclic carbene skeleton (e.g., an imidazolium skeleton, a benzimidazolium skeleton, and a triazolium skeleton), and the like.

The organometallic complex of one embodiment of the present invention can also be represented by the following general formula (G2).

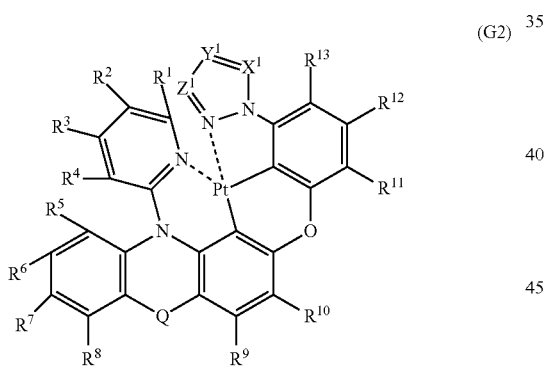

(G2)

In the above general formula (G2), each of $R^1$ to $R^{13}$ independently represents any of hydrogen, a substituted or unsubstituted alkyl group having 1 to 6 carbon atoms, and a substituted or unsubstituted phenyl group, and each of $X^1$, $Y^1$, and $Z^1$ independently represents a nitrogen atom or a carbon atom. Note that none or one of $X^1$, $Y^1$, and $Z^1$ represents a nitrogen atom. In addition, Q represents a sulfur atom or an oxygen atom.

Two or three of $X^1$, $Y^1$, and $Z^1$ each represent a carbon atom, and the carbon atom may have a substituent or no substituent. In the case where the carbon atom has a substituent, as the substituent, a substituted or unsubstituted alkyl group having 1 to 6 carbon atoms or a substituted or unsubstituted phenyl group can be used.

The organometallic complex of one embodiment of the present invention can also be represented by the following general formula (G3).

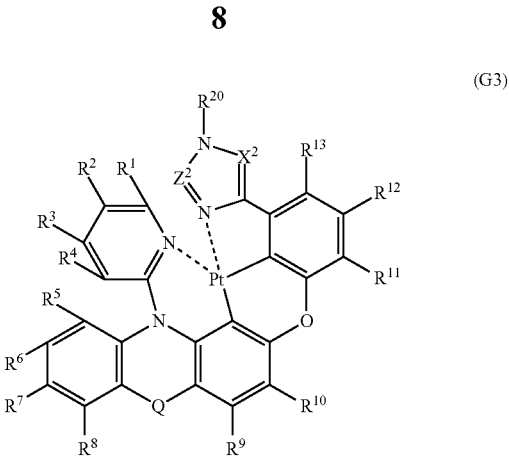

(G3)

In the above general formula (G3), each of $R^1$ to $R^{13}$ and $R^{20}$ independently represents any of hydrogen, a substituted or unsubstituted alkyl group having 1 to 6 carbon atoms, and a substituted or unsubstituted phenyl group, and each of $X^2$ and $Z^2$ independently represents a nitrogen atom or a carbon atom. When one of $X^2$ and $Z^2$ represents a nitrogen atom, the other thereof represents a carbon atom. In addition, Q represents a sulfur atom or an oxygen atom.

When one or both of $X^2$ and $Z^2$ represent a carbon atom, the carbon atom may have a substituent or no substituent. In the case where the carbon atom has a substituent, as the substituent, a substituted or unsubstituted alkyl group having 1 to 6 carbon atoms or a substituted or unsubstituted phenyl group can be used.

The organometallic complex of one embodiment of the present invention can also be represented by the following general formula (G4).

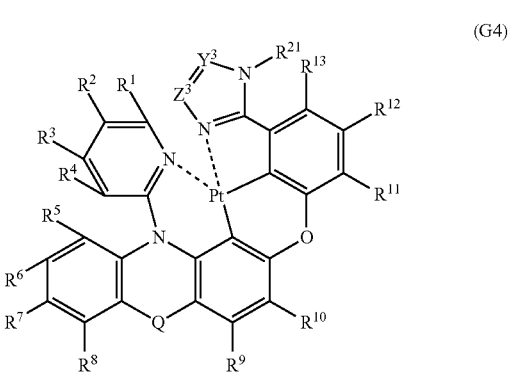

(G4)

In the above general formula (G4), each of $R^1$ to $R^{13}$ and $R^{21}$ independently represents any of hydrogen, a substituted or unsubstituted alkyl group having 1 to 6 carbon atoms, and a substituted or unsubstituted phenyl group, and each of $Y^3$ and $Z^3$ independently represents a nitrogen atom or a carbon atom. When one of $Y^3$ and $Z^3$ represents a nitrogen atom, the other thereof represents a carbon atom. In addition, Q represents a sulfur atom or an oxygen atom.

When one or both of $Y^3$ and $Z^3$ represent a carbon atom, the carbon atom may have a substituent or no substituent. In the case where the carbon atom has a substituent, as the substituent, a substituted or unsubstituted alkyl group having 1 to 6 carbon atoms or a substituted or unsubstituted phenyl group can be used.

The organometallic complex of one embodiment of the present invention can also be represented by the following general formula (G5).

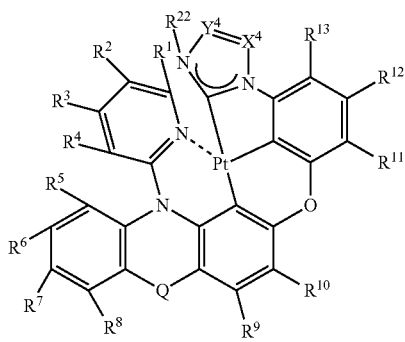

(G5)

In the above general formula (G5), each of $R^1$ to $R^{13}$ and $R^{22}$ independently represents any of hydrogen, a substituted or unsubstituted alkyl group having 1 to 6 carbon atoms, and a substituted or unsubstituted phenyl group, and each of $X^4$ and $Y^4$ independently represents a nitrogen atom or a carbon atom. When one of $X^4$ and $Y^4$ represents a nitrogen atom, the other thereof represents a carbon atom. When one or both of $X^4$ and $Y^4$ represent a carbon atom, the carbon atom may have a substituent or no substituent. In addition, Q represents a sulfur atom or an oxygen atom.

The organometallic complex represented by the above general formula (G5) can also be represented by the following general formulae (G5-1) and (G5-2).

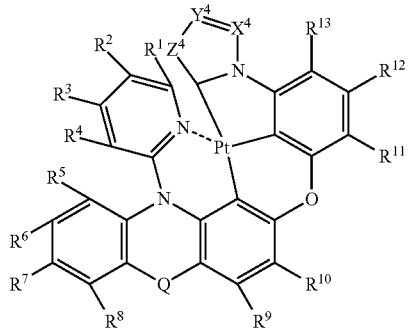

(G5-1)

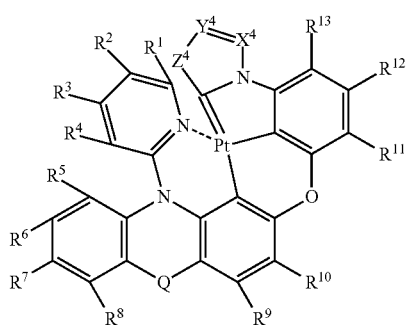

(G5-2)

In the above general formulae (G5-1) and (G5-2), each of $R^1$ to $R^{13}$ independently represents any of hydrogen, a substituted or unsubstituted alkyl group having 1 to 6 carbon atoms, and a substituted or unsubstituted phenyl group, and each of $X^4$, $Y^4$, and $Z^4$ independently represents a nitrogen atom or a carbon atom. Note that one or two of $X^4$, $Y^4$, and $Z^4$ represent a nitrogen atom. In the case where one or two of $X^4$, $Y^4$, and $Z^4$ represent a carbon atom, the carbon atom may have a substituent or no substituent. In addition, Q represents a sulfur atom or an oxygen atom.

The organometallic complex of one embodiment of the present invention can also be represented by the following general formula (G6).

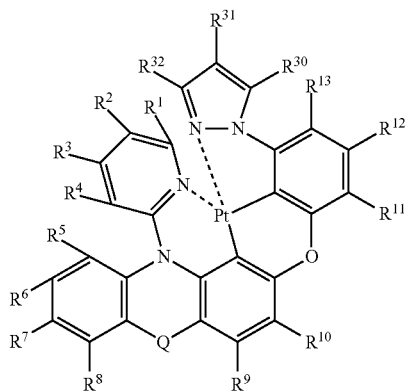

(G6)

In the above general formula (G6), each of $R^1$ to $R^{13}$ and $R^{30}$ to $R^{32}$ independently represents any of hydrogen, a substituted or unsubstituted alkyl group having 1 to 6 carbon atoms, and a substituted or unsubstituted phenyl group, and Q represents a sulfur atom or an oxygen atom.

In the organometallic complex having the above structure, each of $R^{30}$ and $R^{32}$ preferably represents a substituted or unsubstituted alkyl group. Each of $R^{30}$ and $R^{32}$ preferably represents a methyl group, in which case the thermophysical properties and stability of the material are improved.

In the organometallic complex having the above structure, the nitrogen atom of the pyridyl group bonded to nitrogen at the 10-position of the phenothiazine skeleton or the phenoxazine skeleton is coordinated to platinum, which is a central metal. A bulky substituent is preferably present at carbon on the para-position with respect to the nitrogen atom, in which case the thermophysical properties and stability of the material are improved and characteristics for narrowing an emission spectrum and increasing emission efficiency are obtained. Thus, in the organometallic complex represented by the above general formula, $R^3$ is preferably a substituted or unsubstituted alkyl group or a substituted or unsubstituted phenyl group, particularly preferably a substituted or unsubstituted t-butyl group or a substituted or unsubstituted phenyl group.

In the organometallic complex having the above structure, $R^{31}$ is preferably a bulky substituent, in which case the thermophysical properties and stability of the material are improved and characteristics for narrowing an emission spectrum and increasing emission efficiency are obtained. Thus, in the organometallic complex represented by the above general formula (G6), $R^{31}$ is preferably a substituted or unsubstituted alkyl group or a substituted or unsubstituted phenyl group, particularly preferably a substituted or unsubstituted t-butyl group or a substituted or unsubstituted phenyl group.

Note that in the case where the expression "a substituted or unsubstituted alkyl group having 1 to 6 carbon atoms" is used or in the case where an alkyl group having 1 to 6 carbon atoms "may have a substituent" in this specification, a halogeno group, an alkoxy group having 1 to 6 carbon atoms, or the like can be used as a substituent that may be bonded to the alkyl group. Similarly, in the case where the expression "a substituted or unsubstituted phenyl group" is used or in the case where a phenyl group "may have a substituent," an alkyl group having 1 to 6 carbon atoms, a halogeno group, an alkoxy group having 1 to 6 carbon atoms, or the like can be used as a substituent that may be bonded to the phenyl group.

Specific examples of an alkyl group having 1 to 6 carbon atoms include a methyl group, an ethyl group, a propyl group, an isopropyl group, an n-butyl group, a sec-butyl group, an isobutyl group, a tert-butyl group, an n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, and a branched or non-branched hexyl group. In addition, examples of a halogeno group include a fluoro group, a chloro group, a bromo group, and an iodo group. In addition, examples of an alkoxy group having 1 to 6 carbon atoms include a straight-chain or branched-chain alkyloxy group such as a methoxy group, an ethoxy group, a propoxy group, an isopropoxy group, a butoxy group, an isobutoxy group, a tert-butoxy group, a pentyloxy group, and a hexyloxy group, and an alkenyloxy group such as a vinyloxy group, a propenyloxy group, a butenyloxy group, a pentenyloxy group, and a hexenyloxy group.

Specific examples of a substituted or unsubstituted phenyl group are a phenyl group, a 2-methylphenyl group, a 2,5-dimethylphenyl group, a 2,6-dimethylphenyl group, a 2,6-diethylphenyl group, a 2,6-diisopropylphenyl group, a 2,6-diisobutylphenyl group, a 2,6-dicyclopropylphenyl group, a 2,4,6-trimethylphenyl group, a 4-fluorophenyl group, a 2,6-difluorophenyl group, a 4-trifluoromethylphenyl group, a 4-cyanophenyl group, a 4-methoxyphenyl group, a 3,4-dimethoxyphenyl group, a 3,4-methylenedioxyphenyl group, a 4-trifluoromethoxyphenyl group, a 4-dimethylaminophenyl group, and the like.

Some specific examples of the organometallic complexes of embodiments of the present invention with the above-described structures are shown below.

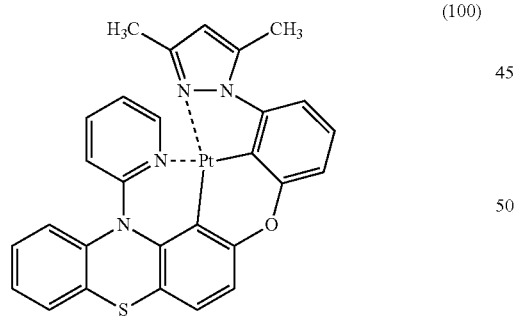
(100)

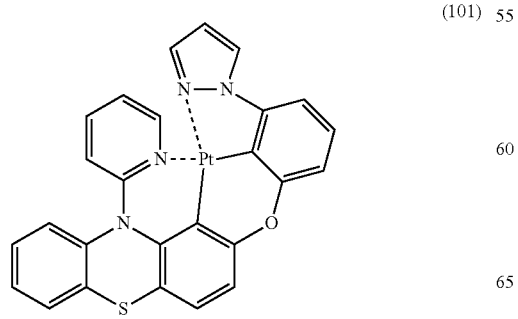
(101)

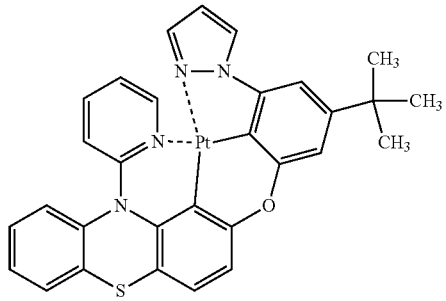
(102)

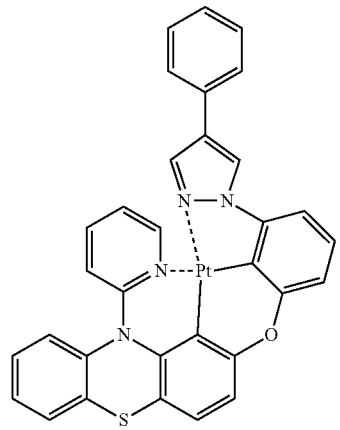
(103)

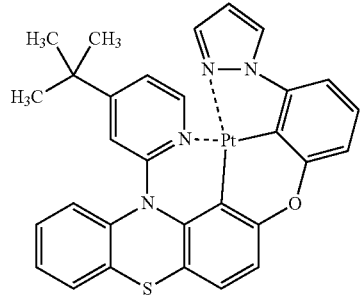
(104)

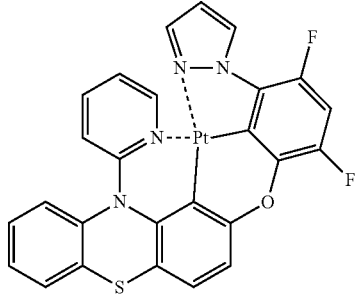
(105)

(106) 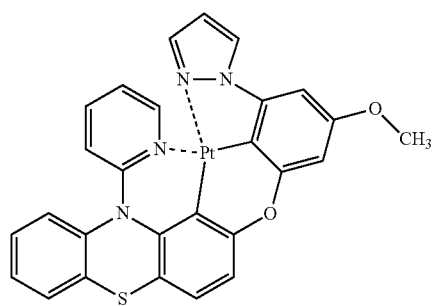
(107) 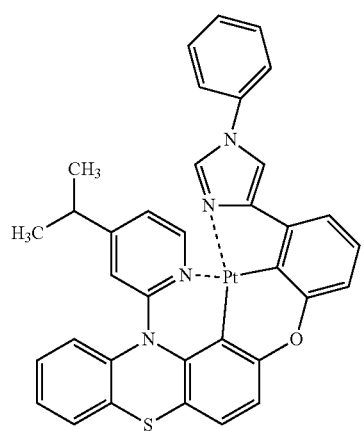
(108) 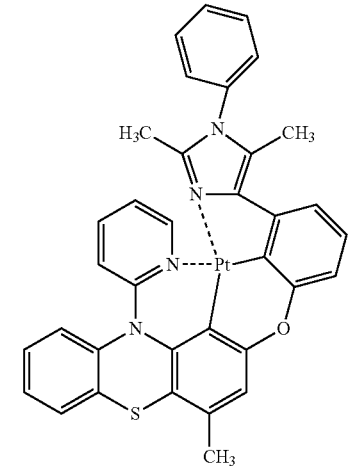
(109) 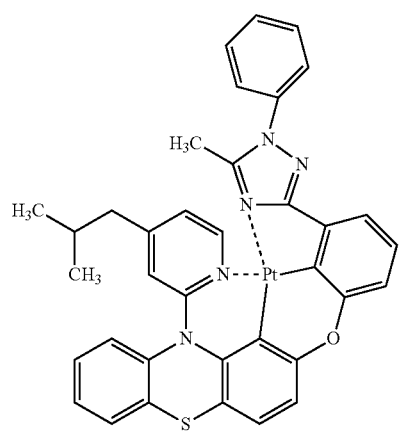
(110) 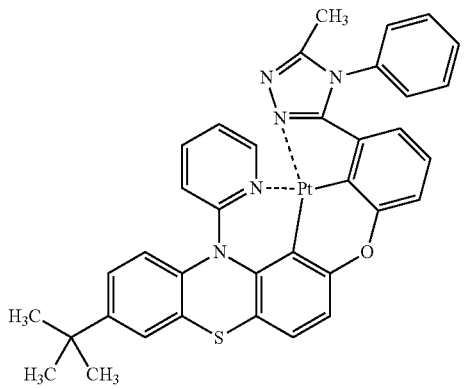
(111) 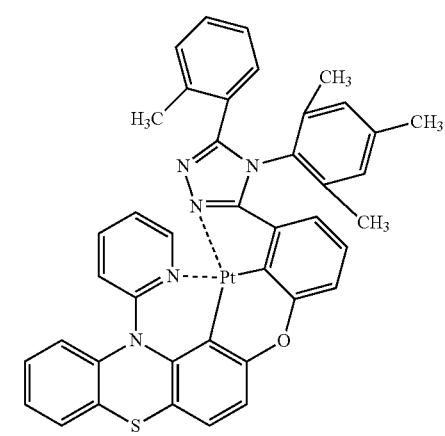
(112) 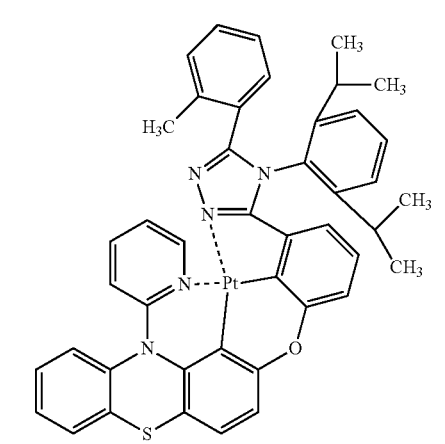
(113) 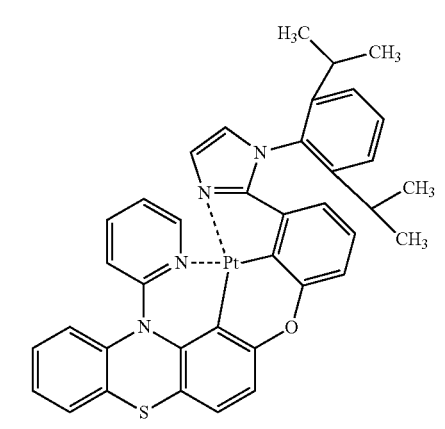

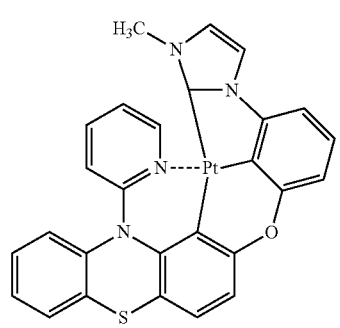
(114)
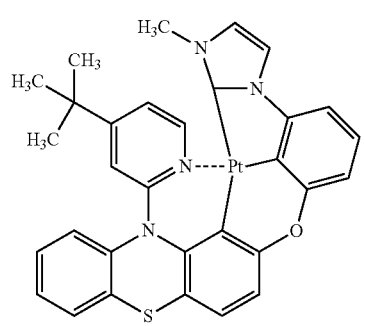
(115)
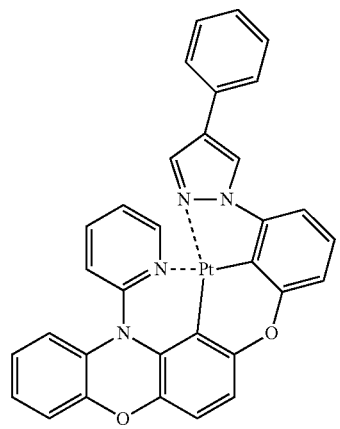
(116)
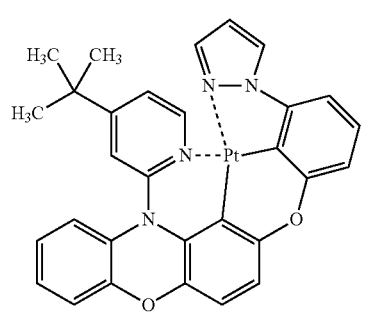
(117)
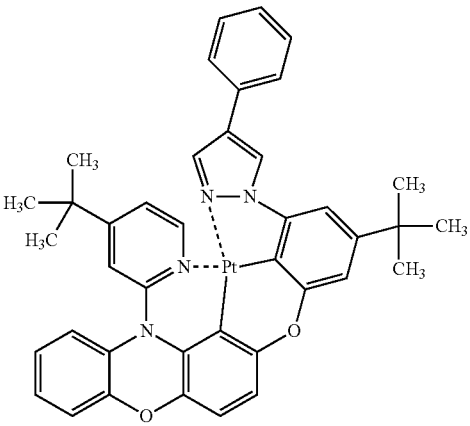
(118)
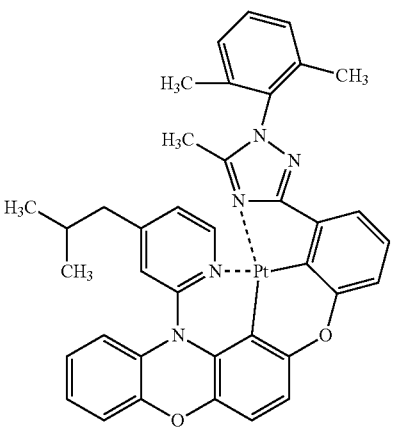
(119)
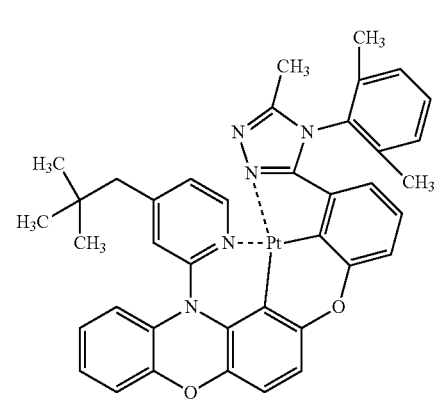
(120)

-continued

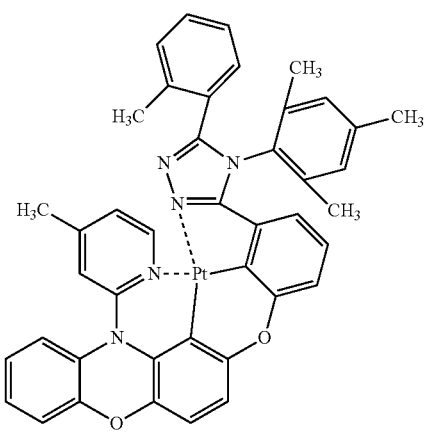

(121)

An example of a method of synthesizing the above-described organometallic complex of one embodiment of the present invention is described.

<Method of Synthesizing Phenothiazine Derivative or Phenoxazine Derivative>

First, an example of a method of synthesizing a phenothiazine derivative or a phenoxazine derivative represented by a general formula (G0) below is described. In the general formula (G0), each of $R^1$ to $R^{13}$ independently represents any of hydrogen, a substituted or unsubstituted alkyl group having 1 to 6 carbon atoms, and a substituted or unsubstituted phenyl group, A represents a five-membered heteroaromatic skeleton including two or three nitrogen atoms, and Q represents sulfur or oxygen.

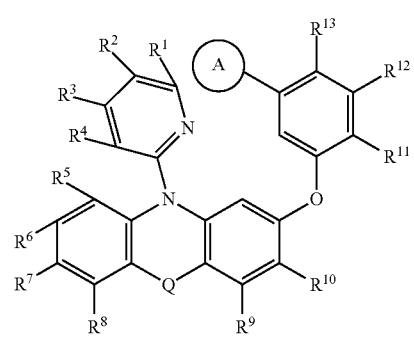

(G0)

As illustrated in a scheme below, a hydroxy compound (A1) and a halide (A2) are reacted, whereby the phenothiazine derivative or the phenoxazine derivative can be obtained. In the scheme below, X represents a halogen, each of $R^1$ to $R^{13}$ independently represents any of hydrogen, a substituted or unsubstituted alkyl group having 1 to 6 carbon atoms, and a substituted or unsubstituted phenyl group, and A represents a five-membered heteroaromatic skeleton including two or three nitrogen atoms. Note that the method of synthesizing the phenothiazine derivative or the phenoxazine derivative is not limited to the scheme below. For example, (A1) may be an alkoxide compound instead of the hydroxy compound, or alternatively, (A1) may be a halide and (A2) may be a hydroxy compound.

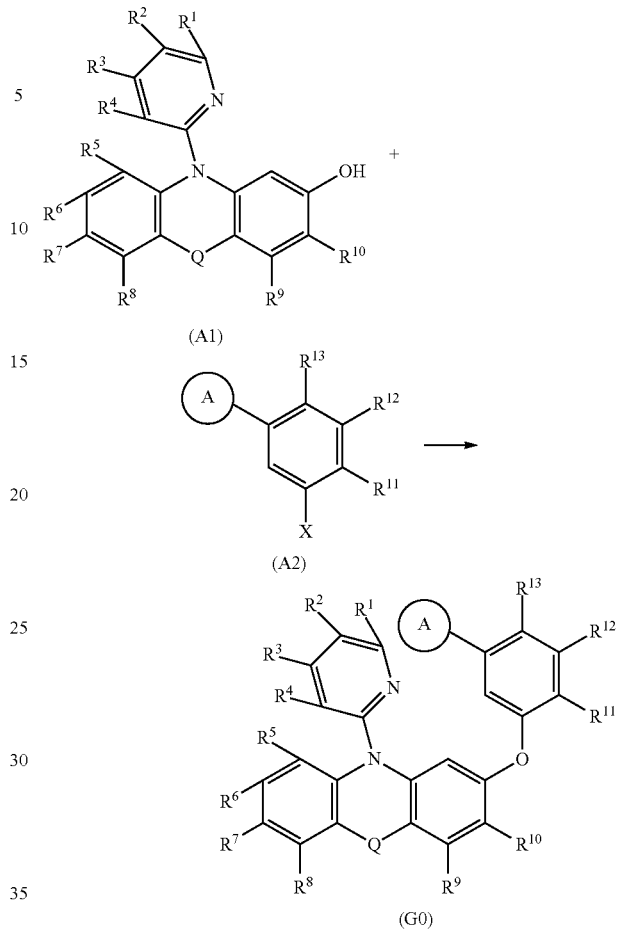

In the above manner, the phenothiazine derivative or the phenoxazine derivative can be synthesized under a very simple synthesis scheme.

<<Method of Synthesizing Organometallic Complex which is One Embodiment of the Present Invention and Represented by General Formula (G1)>>

First, as illustrated in a synthesis scheme below, a mixed solution of the phenothiazine derivative or the phenoxazine derivative represented by the general formula (G0), potassium tetrachloroplatinate, and acetic acid or a solvent containing acetic acid is heated in an inert gas atmosphere, whereby the organometallic complex which is one embodiment of the present invention and represented by the general formula (G1) can be obtained.

potassium tetrachloroplatinate +

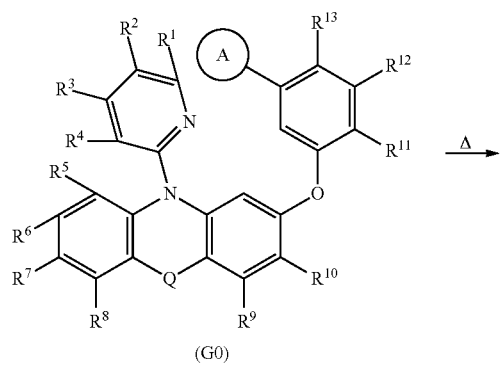

-continued

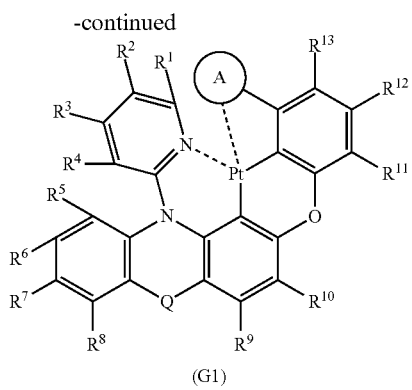

(G1)

In the synthesis scheme above, each of $R^1$ to $R^{13}$ independently represents any of hydrogen, a substituted or unsubstituted alkyl group having 1 to 6 carbon atoms, and a substituted or unsubstituted phenyl group, and A represents a five-membered heteroaromatic skeleton including two or three nitrogen atoms.

<<Light-Emitting Element>>

Next, an example of a light-emitting element which is one embodiment of the present invention is described in detail below with reference to FIG. 1A.

In this embodiment, the light-emitting element includes a pair of electrodes (a first electrode 101 and a second electrode 102), and an EL layer 103 provided between the first electrode 101 and the second electrode 102. Note that the first electrode 101 functions as an anode and the second electrode 102 functions as a cathode.

To function as an anode, the first electrode 101 is preferably formed using any of metals, alloys, conductive compounds having a high work function (specifically, a work function of 4.0 eV or more), mixtures thereof, and the like. Specific examples include indium oxide-tin oxide (ITO: indium tin oxide), indium oxide-tin oxide containing silicon or silicon oxide, indium oxide-zinc oxide, and indium oxide containing tungsten oxide and zinc oxide (IWZO). Films of such conductive metal oxides are usually formed by a sputtering method, but may be formed by application of a sol-gel method or the like. In an example of the formation method, indium oxide-zinc oxide is deposited by a sputtering method using a target obtained by adding 1 wt % to 20 wt % of zinc oxide to indium oxide. Furthermore, a film of indium oxide containing tungsten oxide and zinc oxide (IWZO) can be formed by a sputtering method using a target in which tungsten oxide and zinc oxide are added to indium oxide at 0.5 wt % to 5 wt % and 0.1 wt % to 1 wt %, respectively. Other examples are gold (Au), platinum (Pt), nickel (Ni), tungsten (W), chromium (Cr), molybdenum (Mo), iron (Fe), cobalt (Co), copper (Cu), palladium (Pd), nitrides of metal materials (e.g., titanium nitride), and the like. Graphene can also be used. Note that when a composite material described later is used for a layer which is in contact with the first electrode 101 in the EL layer 103, an electrode material can be selected regardless of its work function.

It is preferable that the EL layer 103 have a stacked-layer structure and any of the layers of the stacked-layer structure contain the organometallic complex represented by any one of the general formulae (G1) to (G6) above.

The stacked-layer structure of the EL layer 103 can be formed by combining a hole-injection layer, a hole-transport layer, a light-emitting layer, an electron-transport layer, an electron-injection layer, a carrier-blocking layer, an intermediate layer, and the like as appropriate. In this embodiment, the EL layer 103 has a structure in which a hole-injection layer 111, a hole-transport layer 112, a light-emitting layer 113, an electron-transport layer 114, and an electron-injection layer 115 are stacked in this order over the first electrode 101. Specific examples of the materials forming the layers are given below.

The hole-injection layer 111 is a layer that contains a substance with a high hole-injection property. Molybdenum oxide, vanadium oxide, ruthenium oxide, tungsten oxide, manganese oxide, or the like can be used. Alternatively, the hole-injection layer 111 can be formed using a phthalocyanine-based compound such as phthalocyanine (abbreviation: $H_2Pc$) or copper phthalocyanine (abbreviation: CuPc), an aromatic amine compound such as 4,4'-bis[N-(4-diphenylaminophenyl)-N-phenylamino]biphenyl (abbreviation: DPAB) or N,N'-bis{4-[bis(3-methylphenyl)amino]phenyl}-N,N'-diphenyl-(1,1'-biphenyl)-4,4'-diamine (abbreviation: DNTPD), a high molecular compound such as poly(3,4-ethylenedioxythiophene)/poly(styrenesulfonic acid) (PEDOT/PSS), or the like.

Alternatively, a composite material in which a substance with a hole-transport property contains a substance with an acceptor property can be used for the hole-injection layer 111. Note that the use of such a substance with a hole-transport property which contains a substance with an acceptor property enables selection of a material used to form an electrode regardless of its work function. In other words, besides a material having a high work function, a material having a low work function can be used for the first electrode 101. As examples of the substance having an acceptor property, 7,7,8,8-tetracyano-2,3,5,6-tetrafluoroquinodimethane (abbreviation: $F_4$-TCNQ), chloranil, and the like can be given. In addition, transition metal oxides can be given. Moreover, oxides of metals belonging to Groups 4 to 8 of the periodic table can be given. Specifically, it is preferable to use vanadium oxide, niobium oxide, tantalum oxide, chromium oxide, molybdenum oxide, tungsten oxide, manganese oxide, and rhenium oxide because of their high electron accepting properties. In particular, molybdenum oxide is more preferable because of its stability in the atmosphere, low hygroscopic property, and easiness of handling.

As the substance with a hole-transport property which is used for the composite material, any of a variety of organic compounds such as aromatic amine compounds, carbazole derivatives, aromatic hydrocarbons, and high molecular compounds (e.g., oligomers, dendrimers, or polymers) can be used. Note that the substance with a hole-transport property which is used for the composite material is preferably a substance having a hole mobility of $10^{-6}$ cm$^2$/Vs or more. Organic compounds that can be used as the substance with a hole-transport property in the composite material are specifically given below.

Examples of the aromatic amine compounds that can be used for the composite material are N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), 1,3,5-tris[N-(4-diphenylaminophenyl)-N-phenylamino]benzene (abbreviation: DPA3B), and the like. Specific examples of the carbazole derivatives are 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenlanino]-9-phenylcarbazole (abbreviation: PCzPCA2), 3-[N-(1-naphthyl)-N-(9-phenylcarbazol-3-yl)amino]-9- phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 1,4-bis[4-(N-carbazolyl)phenyl]-2,3,5,6-tetraphenylbenzene, and the like. Examples of the aromatic hydrocarbons are 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Besides, pentacene, coronene, or the like can also be used. The aromatic hydrocarbons may have a vinyl skeleton. Examples of the aromatic hydrocarbon having a vinyl skeleton are 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

A high molecular compound such as poly(N-vinylcarbazole) (abbreviation: PVK), poly(4-vinyltriphenylamine) (abbreviation: PVTPA), poly[N-(4-{N-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: poly-TPD) can also be used.

By providing the hole-injection layer, a high hole-injection property can be achieved to allow a light-emitting element to be driven at a low voltage.

Note that the hole-injection layer may be formed of the above-described acceptor material alone or of the above-described acceptor material and another material in combination. In this case, the acceptor material extracts electrons from the hole-transport layer, so that holes can be injected into the hole-transport layer. The acceptor material transfers the extracted electrons to the anode.

The hole-transport layer 112 is a layer that contains a substance with a hole-transport property. Examples of the substance with a hole-transport property are aromatic amine compounds such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), and the like. The substances mentioned here have high hole-transport properties and are mainly ones that have a hole mobility of $10^{-6}$ cm$^2$/Vs or more. An organic compound given as an example of the substance with a hole-transport property in the composite material described above can also be used for the hole-transport layer 112. A high molecular compound such as poly(N-vinylcarbazole) (abbreviation: PVK) or poly(4-vinyltriphenylamine) (abbreviation: PVTPA) can also be used. Note that the layer that contains a substance with a hole-transport property is not limited to a single layer, and may be a stack of two or more layers including any of the above substances.

The light-emitting layer 113 may be a layer that emits fluorescence, a layer that emits phosphorescence, or a layer emitting thermally activated delayed fluorescence (TADF). Furthermore, the light-emitting layer 113 may be a single layer or include a plurality of layers containing different light-emitting substances. In the case where the light-emitting layer including a plurality of layers is formed, a layer containing a phosphorescent substance and a layer containing a fluorescent substance may be stacked. In that case, an exciplex described later is preferably utilized for the layer containing the phosphorescent substance.

As the fluorescent substance, any of the following substances can be used, for example. Fluorescent substances other than those given below can also be used. Examples of the fluorescent substance are 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4- ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and the like. Condensed aromatic diamine compounds typified by pyrenediamine compounds such as 1,6FLPAPrn and 1,6mMemFLPAPrn are preferable because of their high hole-trapping properties, high emission efficiency, and high reliability.

Examples of a material which can be used as a phosphorescent substance in the light-emitting layer 113 are as follows. The examples include organometallic iridium complexes having 4H-triazole skeletons, such as tris{2-[5-(2-methylphenyl)-4-(2,6-dimethylphenyl)-4H-1,2,4-triazol-3-yl-κN$^2$]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), and tris[4-(3-biphenyl)-5-isopropyl-3-phenyl-4H-1,2,4-triazolato]iridium(III) (abbreviation: [Ir(iPrptz-3b)$_3$]); organometallic iridium complexes having 1H-triazole skeletons, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); organometallic iridium complexes having imidazole skeletons, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-J]phenanthridinato]iridium(III) (abbreviation: [Ir(dmpimpt-Me)$_3$]); and organometallic iridium complexes in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^2$}iridium(III) picolinate (abbreviation: [Ir(CF$_3$ppy)$_2$(pic)]), and bis[2-(4',6'-difluorophenyl)pyridinato-N,C$^{2'}$]iridium(III) acetylacetonate (abbreviation: FIr(acac)). These are compounds emitting blue phosphorescence and have an emission peak at 440 nm to 520 nm.

Other examples include organometallic iridium complexes having pyrimidine skeletons, such as tris(4-methyl-6-phenylpyrimidinato)iridium(III) (abbreviation: [Ir(mppm)$_3$]), tris(4-t-butyl-6-phenylpyrinidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), and (acetylacetonato)bis(4,6-diphenylpyrimidinato)iridium(III) (abbreviation: [Ir(dppm)$_2$(acac)]); organometallic iridium complexes having pyrazine skeletons, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having pyridine skeletons, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), and bis(2-phenylquinolinato-N,C$^{2'}$)iridium(III) acetylacetonate (abbreviation: [Ir(pq)$_2$(acac)]); and rare earth metal complexes such as tris(acetylacetonato)(monophenanthroline)terbium(III) (abbreviation: [Tb(acac)$_3$(Phen)]). These are mainly compounds emitting green phosphorescence and have an emission peak at 500 nm to 600 nm. Note that organometallic iridium complexes having pyrimidine skeletons have distinctively high reliability and emission efficiency and thus are especially preferable.

Other examples include organometallic iridium complexes having pyrimidine skeletons, such as (diisobutyryhnethanato)bis[4,6-bis(3-methylphenyl)pyrimnidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and bis[4,6-di(naphthalen-1-yl)pyrimidinato](dipivaloylmethanato)iridium(III) (abbreviation: [Ir(dlnpm)$_2$(dpm)]); organometallic iridium complexes having pyrazine skeletons, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), and (acetylacetonato)bis[2,3-bis(4-fluorophenyl)quinoxalinato]iridium(III) (abbreviation: [Ir(Fdpq)$_2$(acac)]); organometallic iridium complexes having pyridine skeletons, such as tris(1-phenylisoquinolinato-N,C$^{2'}$)iridium(II) (abbreviation: [Ir(piq)$_3$]) and bis(1-phenylisoquinolinato-N,C$^{2'}$)iridium(III) acetylacetonate (abbreviation: [Ir(piq)$_2$(acac)]); platinum complexes such as 2,3,7,8,12,13,17,18-octaethyl-21H,23H-porphyrin platinum(II) (abbreviation: PtOEP); and rare earth metal complexes such as tris(1,3-diphenyl-1,3-propanedionato)(monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]). These are compounds emitting red phosphorescence and have an emission peak at 600 nm to 700 nm. Furthermore, organometallic iridium complexes having pyrazine skeletons can provide red light emission with favorable chromaticity.

As well as the above phosphorescent compounds, a variety of phosphorescent substances may be selected and used.

Note that the organometallic complex of one embodiment of the present invention is preferably used as the phosphorescent substance. The organometallic complex of one embodiment of the present invention emits light efficiently, resulting in high emission efficiency of a light-emitting element.

Examples of the TADF material include a fullerene, a derivative thereof, an acridine derivative such as proflavine, and eosin. Furthermore, a metal-containing porphyrin, such as a porphyrin containing magnesium (Mg), zinc (Zn), cadmium (Cd), tin (Sn), platinum (Pt), indium (In), or palladium (Pd) can be used. Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$(OEP)), which are shown in the following structural formulae.

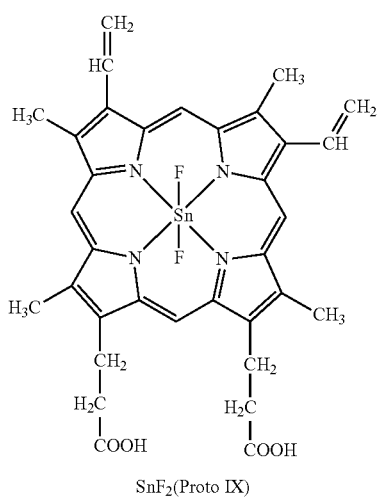
SnF$_2$(Proto IX)
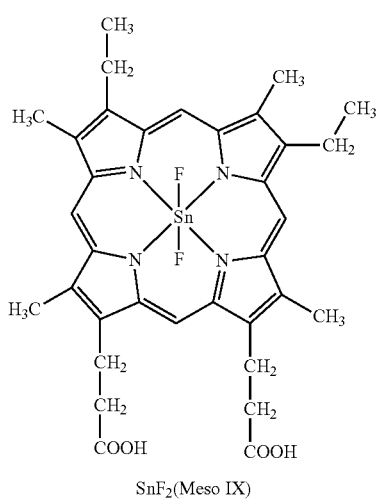
SnF$_2$(Meso IX)
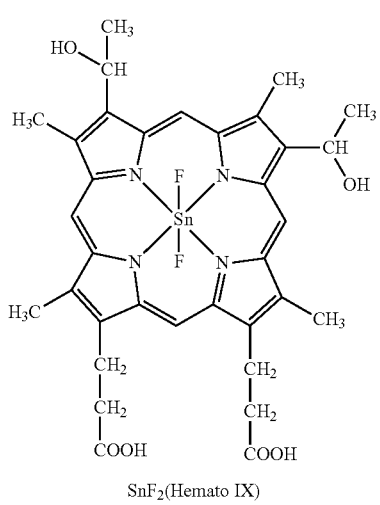
SnF$_2$(Hemato IX)
-continued
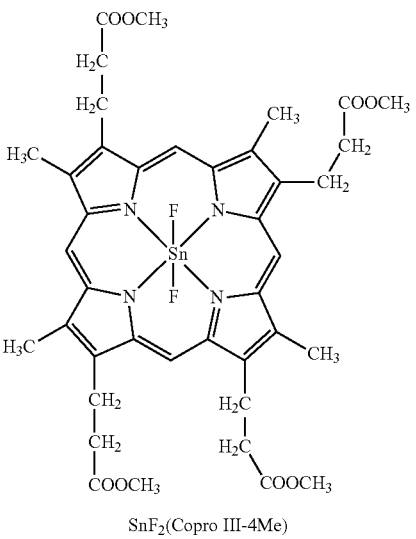
SnF$_2$(Copro III-4Me)
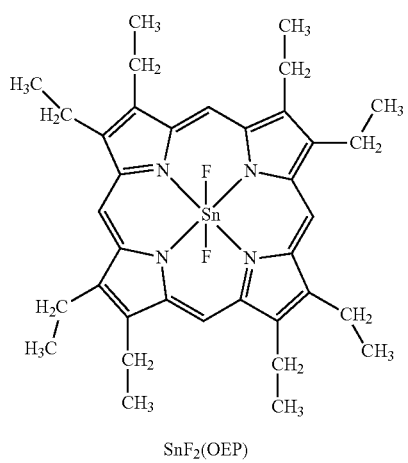
SnF$_2$(OEP)
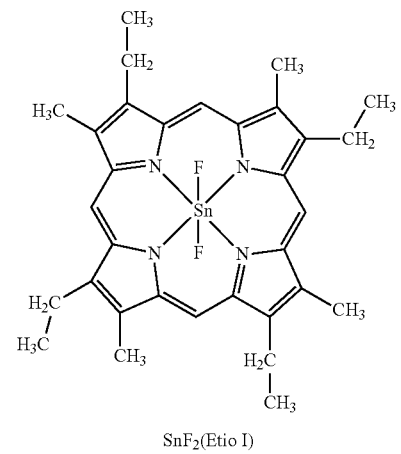
SnF$_2$(Etio I)

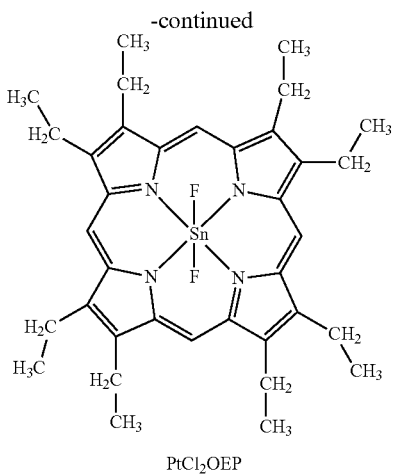

PtCl₂OEP

Alternatively, a heterocyclic compound having a π-electron rich heteroaromatic ring and a π-electron deficient heteroaromatic ring, such as 2-(biphenyl-4-yl)-4,6-bis(12-phenylindolo[2,3-a]carbazol-11-yl)-1,3,5-triazine (abbreviation: PIC-TRZ) shown in the following structural formula, can be used. The heterocyclic compound is preferably used because of the π-electron rich heteroaromatic ring and the π-electron deficient heteroaromatic ring, for which the electron-transport property and the hole-transport property are high. Note that a substance in which the π-electron rich heteroaromatic ring is directly bonded to the π-electron deficient heteroaromatic ring is particularly preferably used because the donor property of the π-electron rich heteroaromatic ring and the acceptor property of the π-electron deficient heteroaromatic ring are both high and the energy difference between the $S_1$ level and the $T_1$ level becomes small.

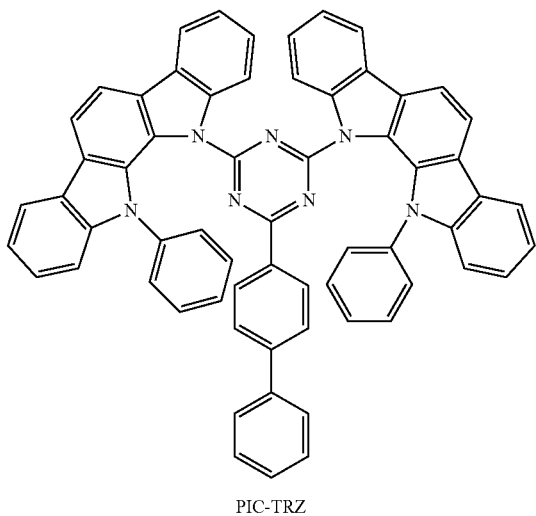 [SMILES: c1ccc(-c2ccc(-c3nc(-n4c5ccccc5c5ccc6c7ccccc7n(-c7ccccc7)c6c54)nc(-n4c5ccccc5c5ccc6c7ccccc7n(-c7ccccc7)c6c54)n3)cc2)cc1]

PIC-TRZ

As a host material of the light-emitting layer, various carrier-transport materials, such as a material with an electron-transport property or a material with a hole-transport property, can be used.

Examples of the material with an electron-transport property are a metal complex such as bis(10-hydroxybenzo[h]quinolinato)beryllium(II) (abbreviation: BeBq₂), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato] zinc(II) (abbreviation: ZnBTZ); a heterocyclic compound having a polyazole skeleton such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-1H-benzimidazole) (abbreviation: TPBI), or 2-[3-(dibenzothiophen-4-yl)phenyl]-1-phenyl-1H-benzimidazole (abbreviation: mDBTBIm-II); a heterocyclic compound having a diazine skeleton such as 2-[3-(dibenzothiophen-4-yl)phenyl]dibenzo[f,h]quinoxaline (abbreviation: 2mDBTP-DBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), or 4,6-bis[3-(4-dibenzothienyl)phenyl]pyrimidine (abbreviation: 4,6mDBTP2Pm-II); and a heterocyclic compound having a pyridine skeleton such as 3,5-bis[3-(9H-carbazol-9-yl)phenyl]pyridine (abbreviation: 35DCzPPy) or 1,3,5-tri[3-(3-pyridyl)phenyl]benzene (abbreviation: TmPyPB). Among the above materials, a heterocyclic compound having a diazine skeleton and a heterocyclic compound having a pyridine skeleton have high reliability and are thus preferable. Specifically, a heterocyclic compound having a diazine (pyrimidine or pyrazine) skeleton has a high electron-transport property to contribute to a reduction in drive voltage.

Examples of the material with a hole-transport property include a compound having an aromatic amine skeleton such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), or N-phenyl-N-[4-(9-phenyl-9H-carbazol-3-yl)phenyl]spiro-9,9'-bifluoren-2-amine (abbreviation: PCBASF); a compound having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), or 3,3'-bis(9-phenyl-9H-carbazole) (abbreviation: PCCP); a compound having a thiophene skeleton such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), or 4-[4-(9-phenyl-9H-fluoren-9-yl)phenyl]-6-phenyldibenzothiophene (abbreviation: DBTFLP-IV); and a compound having a furan skeleton such as 4,4',4''-(benzene-1,3,5-triyl)tri(dibenzofuran) (abbreviation: DBF3P-II) or 4-{3-[3-(9-phenyl-9H-fluoren-9-yl)phenyl]phenyl}dibenzofuran (abbreviation: mmDBFFLBi-II).

Among the above materials, a compound having an aromatic amine skeleton and a compound having a carbazole skeleton are preferable because these compounds are highly reliable and have high hole-transport properties to contribute to a reduction in drive voltage. Hole-transport materials can be selected from a variety of substances as well as from the hole-transport materials given above.

In the case of using a fluorescent substance as a light-emitting substance, materials that can be suitably used are materials having an anthracene skeleton such as 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), and 9-phenyl-10-{4-(9-phenyl-9H-fluoren-9-yl)biphenyl-4'-yl}anthracene (abbreviation: FLPPA). The use of a substance having an anthracene skeleton as the host material for the fluorescent substance makes it possible to obtain a light-emitting layer with high emission efficiency and high durability. In particular, CzPA, cgDBCzPA, 2mBnfPPA, and PCzPA are preferable because of their excellent characteristics.

Note that the host material may be a mixture of a plurality of kinds of substances, and in the case of using a mixed host material, it is preferable to mix a material having an electron-transport property with a material having a hole-transport property. By mixing the material having an electron-transport property with the material having a hole-transport property, the transport property of the light-emitting layer 113 can be easily adjusted and a recombination region can be easily controlled. The ratio of the content of the material having a hole-transport property to the content of the material having an electron-transport property may be 1:9 to 9:1.

These mixed host materials may form an exciplex. When a combination of these materials is selected so as to form an exciplex that exhibits light emission whose wavelength overlaps the wavelength of a lowest-energy-side absorption band of the fluorescent substance, the phosphorescent substance, or the TADF material, energy is transferred smoothly and light emission can be obtained efficiently. Such a structure is preferable in that drive voltage can be reduced.

The light-emitting layer 113 having the above-described structure can be formed by co-evaporation by a vacuum evaporation method, or a gravure printing method, an offset printing method, an inkjet method, a spin coating method, a dip coating method, or the like using a solution of the materials.

The electron-transport layer 114 contains a substance with an electron-transport property. As the substance with an electron-transport property, the materials having an electron-transport property or having an anthracene skeleton, which are described above as materials for the host material, can be used.

Between the electron-transport layer and the light-emitting layer, a layer that controls transport of electron carriers may be provided. This is a layer formed by addition of a small amount of a substance having a high electron-trapping property to the aforementioned material having a high electron-transport property, and the layer is capable of adjusting carrier balance by retarding transport of electron carriers. Such a structure is very effective in preventing a problem (such as a reduction in element lifetime) caused when electrons pass through the light-emitting layer.

In addition, the electron-injection layer 115 may be provided in contact with the second electrode 102 between the electron-transport layer 114 and the second electrode 102. For the electron-injection layer 115, an alkali metal, an alkaline earth metal, or a compound thereof, such as lithium fluoride (LiF), cesium fluoride (CsF), or calcium fluoride ($CaF_2$), can be used. For example, a layer that is formed using a substance having an electron-transport property and contains an alkali metal, an alkaline earth metal, or a compound thereof can be used. In addition, an electride may be used for the electron-injection layer 115. Examples of the electride include a substance in which electrons are added at high concentration to calcium oxide-aluminum oxide. Note that a layer that is formed using a substance having an electron-transport property and contains an alkali metal or an alkaline earth metal is preferably used as the electron-injection layer 115, in which case electron injection from the second electrode 102 is efficiently performed.

Figure 1B:
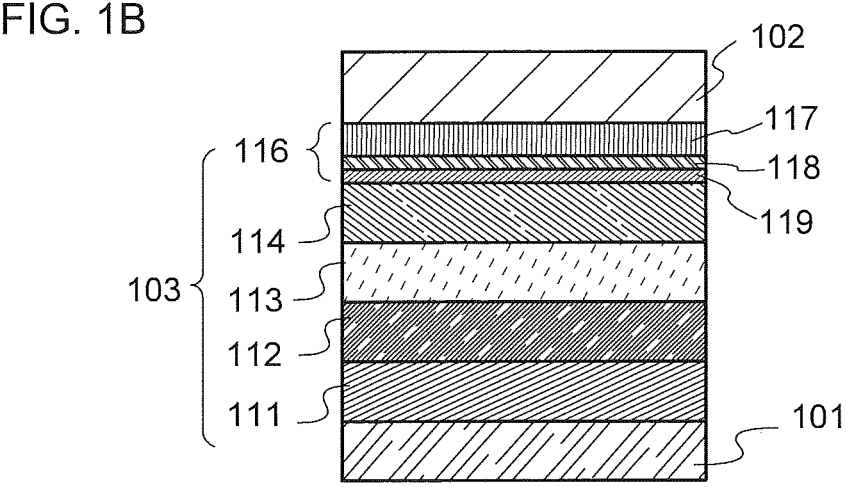

Instead of the electron-injection layer 115, a charge-generation layer 116 may be provided (FIG. 1B). The charge-generation layer 116 refers to a layer capable of injecting holes into a layer in contact with the cathode side of the charge-generation layer 116 and electrons into a layer in contact with the anode side thereof when a potential is applied. The charge-generation layer 116 includes at least a p-type layer 117. The p-type layer 117 is preferably formed using any of the composite materials given above as examples of materials that can be used for the hole-injection layer 111. The p-type layer 117 may be formed by stacking a film containing the above-described acceptor material as a material included in the composite material and a film containing the above-described hole-transport material. When a potential is applied to the p-type layer 117, electrons are injected into the electron-transport layer 114 and holes are injected into the second electrode 102 serving as a cathode; thus, the light-emitting element operates. When a layer containing the organic compound of one embodiment of the present invention exists in the electron-transport layer 114 so as to be in contact with the charge-generation layer 116, a luminance decrease due to accumulation of driving time of the light-emitting element can be suppressed, and thus, the light-emitting element can have a long lifetime.

Note that the charge-generation layer 116 preferably includes either an electron-relay layer 118 or an electron-injection buffer layer 119 or both in addition to the p-type layer 117.

The electron-relay layer 118 contains at least the substance with an electron-transport property and has a function of preventing an interaction between the electron-injection buffer layer 119 and the p-type layer 117 and smoothly transferring electrons. The LUMO level of the substance with an electron-transport property contained in the electron-relay layer 118 is preferably between the LUMO level of an acceptor substance in the p-type layer 117 and the LUMO level of a substance contained in a layer of the electron-transport layer 114 in contact with the charge-generation layer 116. As a specific value of the energy level, the LUMO level of the substance with an electron-transport property contained in the electron-relay layer 118 is preferably higher than or equal to −5.0 eV, more preferably higher than or equal to −5.0 eV and lower than or equal to −3.0 eV. Note that as the substance with an electron-transport property in the electron-relay layer 118, a phthalocyanine-based material or a metal complex having a metal-oxygen bond and an aromatic ligand is preferably used.

A substance having a high electron-injection property can be used for the electron-injection buffer layer 119. For example, an alkali metal, an alkaline earth metal, a rare earth metal, or a compound thereof (e.g., an alkali metal compound (including an oxide such as lithium oxide, a halide, and a carbonate such as lithium carbonate or cesium carbonate), an alkaline earth metal compound (including an oxide, a halide, and a carbonate), or a rare earth metal compound (including an oxide, a halide, and a carbonate)) can be used.

In the case where the electron-injection buffer layer 119 contains the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, a compound of the above metal (e.g., an alkali metal compound (including an oxide such as lithium oxide, a halide, and a carbonate such as lithium carbonate or cesium carbonate), an alkaline earth metal compound (including an oxide, a halide, and a carbonate), and a rare earth metal compound (including an oxide, a halide, and a carbonate)). Note that as the substance having an electron-transport property, a material similar to the above-described material used for the electron-transport layer 114 can be used. Furthermore, the organic compound of the present invention can be used.

For the second electrode 102, any of metals, alloys, electrically conductive compounds, and mixtures thereof which have a low work function (specifically, a work function of 3.8 eV or less) or the like can be used. Specific examples of such a cathode material are elements belonging to Groups 1 and 2 of the periodic table, such as alkali metals (e.g., lithium (Li) and cesium (Cs)), magnesium (Mg), calcium (Ca), and strontium (Sr), alloys thereof (e.g., MgAg and AlLi), rare earth metals such as europium (Eu) and ytterbium (Yb), alloys thereof, and the like. However, when the electron-injection layer is provided between the second electrode 102 and the electron-transport layer, for the second electrode 102, any of a variety of conductive materials such as Al, Ag, ITO, or indium oxide-tin oxide containing silicon or silicon oxide can be used regardless of the work function. Films of these conductive materials can be formed by a dry method such as a vacuum evaporation method or a sputtering method, an inkjet method, a spin coating method, or the like. In addition, the films of these conductive materials may be formed by a wet method using a sol-gel method, or by a wet method using paste of a metal material.

Any of a variety of methods can be used to form the EL layer 103 regardless of whether it is a dry process or a wet process. For example, a vacuum evaporation method, a gravure printing method, an offset printing method, a screen printing method, an inkjet method, a spin coating method, or the like may be used.

In addition, the electrode may be formed by a wet method using a sol-gel method, or by a wet method using paste of a metal material. Alternatively, the electrode may be formed by a dry method such as a sputtering method or a vacuum evaporation method.

Light emission from the light-emitting element is extracted out through one or both of the first electrode 101 and the second electrode 102. Therefore, one or both of the first electrode 101 and the second electrode 102 are formed as a light-transmitting electrode.

The structure of the layers provided between the first electrode 101 and the second electrode 102 is not limited to the above-described structure. Preferably, a light-emitting region where holes and electrons recombine is positioned away from the first electrode 101 and the second electrode 102 so that quenching due to the proximity of the light-emitting region and a metal used for electrodes and carrier-injection layers can be prevented.

Furthermore, in order that transfer of energy from an exciton generated in the light-emitting layer can be suppressed, preferably, the hole-transport layer and the electron-transport layer which are in contact with the light-emitting layer 113, particularly a carrier-transport layer in contact with a side closer to the recombination region in the light-emitting layer 113, are formed using a substance having a wider band gap than the light-emitting substance of the light-emitting layer or the emission center substance included in the light-emitting layer.

Next, a mode of a light-emitting element with a structure in which a plurality of light-emitting units are stacked (this type of light-emitting element is also referred to as a stacked element) is described with reference to FIG. 1C. This light-emitting element includes a plurality of light-emitting units between an anode and a cathode. One light-emitting unit has the same structure as the EL layer 103 illustrated in FIG. 1A. In other words, the light-emitting element illustrated in FIG. 1A or 1B includes a single light-emitting unit, and the light-emitting element illustrated in FIG. 1C includes a plurality of light-emitting units.

Figure 1C:
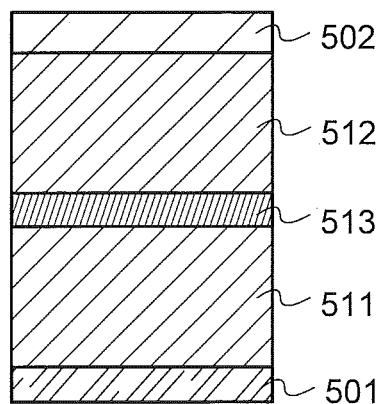

In FIG. 1C, a first light-emitting unit 511 and a second light-emitting unit 512 are stacked between a first electrode 501 and a second electrode 502, and a charge-generation layer 513 is provided between the first light-emitting unit 511 and the second light-emitting unit 512. The first electrode 501 and the second electrode 502 correspond, respectively, to the first electrode 101 and the second electrode 102 illustrated in FIG. 1A, and the materials given in the description for FIG. 1A can be used. Furthermore, the first light-emitting unit 511 and the second light-emitting unit 512 may have the same structure or different structures.

The charge-generation layer 513 has a function of injecting electrons into one of the light-emitting units and injecting holes into the other of the light-emitting units when a voltage is applied between the first electrode 501 and the second electrode 502. That is, in FIG. 1C, the charge-generation layer 513 injects electrons into the first light-emitting unit 511 and holes into the second light-emitting unit 512 when a voltage is applied so that the potential of the first electrode becomes higher than the potential of the second electrode.

The charge-generation layer 513 preferably has a structure similar to the structure of the charge-generation layer 116 described with reference to FIG. 1B. Since the composite material of an organic compound and a metal oxide is superior in carrier-injection property and carrier-transport property, low-voltage driving or low-current driving can be achieved. Note that when a surface of a light-emitting unit on the anode side is in contact with the charge-generation layer 513, the charge-generation layer 513 can also serve as a hole-injection layer of the light-emitting unit; thus, a hole-transport layer is not necessarily formed in the light-emitting unit.

In the case where the electron-injection buffer layer 119 is provided, the electron-injection buffer layer serves as the electron-injection layer in the light-emitting unit on the anode side and the light-emitting unit does not necessarily further need an electron-injection layer.

Note that when a layer in contact with a surface of the charge-generation layer 513 on the anode side in a light-emitting unit (typically, the electron-transport layer in the light-emitting unit on the anode side) contains the organic compound of one embodiment of the present invention which is described in Embodiment, a luminance decrease due to accumulation of driving time can be suppressed, and thus, the light-emitting element can have high reliability.

The light-emitting element having two light-emitting units is described with reference to FIG. 1C; however, the present invention can be similarly applied to a light-emitting element in which three or more light-emitting units are stacked. With a plurality of light-emitting units partitioned by the charge-generation layer 513 between a pair of electrodes as in the light-emitting element according to this embodiment, it is possible to provide an element which can emit light with high luminance with the current density kept low and has a long lifetime. A light-emitting device that can be driven at a low voltage and has low power consumption can be realized.

Furthermore, when emission colors of the light-emitting units are made different, light emission of a desired color can be obtained from the light-emitting element as a whole. For example, it is easy to enable a light-emitting element having two light-emitting units to emit white light as the whole element when the emission colors of the first light-emitting unit are red and green and the emission color of the second light-emitting unit is blue.

<<Micro Optical Resonator (Microcavity) Structure>>

A light-emitting element with a microcavity structure is formed with the use of a reflective electrode and a semi-transmissive and semi-reflective electrode as the pair of electrodes. The reflective electrode and the semi-transmissive and semi-reflective electrode correspond to the first electrode and the second electrode described above. The light-emitting element with a microcavity structure includes at least an EL layer between the reflective electrode and the semi-transmissive and semi-reflective electrode. The EL layer includes at least a light-emitting layer serving as a light-emitting region.

Light emitted from the light-emitting layer included in the EL layer is reflected and resonated by the reflective electrode and the semi-transmissive and semi-reflective electrode. Note that the reflective electrode is formed using a conductive material having reflectivity and has a visible light reflectivity of 40% to 100%, preferably 70% to 100% and a resistivity of $1 \times 10^{-2}$ Ωcm or lower. In addition, the semi-transmissive and semi-reflective electrode is formed using a conductive material having reflectivity and a light-transmitting property and has a visible light reflectivity of 20% to 80%, preferably 40% to 70%, and a resistivity of $1 \times 10^{-2}$ Ωcm or lower.

In the light-emitting element, by changing thicknesses of the transparent conductive film, the composite material, the carrier-transport material, and the like, the optical path length between the reflective electrode and the semi-transmissive and semi-reflective electrode can be changed. Thus, light with a wavelength that is resonated between the reflective electrode and the semi-transmissive and semi-reflective electrode can be intensified while light with a wavelength that is not resonated therebetween can be attenuated.

Note that light that is emitted from the light-emitting layer and reflected back by the reflective electrode (first reflected light) considerably interferes with light that directly enters the semi-transmissive and semi-reflective electrode from the light-emitting layer (first incident light). For this reason, the optical path length between the reflective electrode and the light-emitting layer is preferably adjusted to $(2n-1)\lambda/4$ (n is a natural number of 1 or larger and λ is a wavelength of color to be amplified). In that case, the phases of the first reflected light and the first incident light can be aligned with each other and the light emitted from the light-emitting layer can be further amplified.

Note that in the above structure, the EL layer may be formed of light-emitting layers or may be a single light-emitting layer. The tandem light-emitting element described above may be combined with the EL layers; for example, a light-emitting element may have a structure in which a plurality of EL layers is provided, a charge-generation layer is provided between the EL layers, and each EL layer is formed of light-emitting layers or a single light-emitting layer.

<<Light-Emitting Device>>

A light-emitting device of one embodiment of the present invention is described using FIGS. 2A and 2B. Note that FIG. 2A is a top view illustrating the light-emitting device and FIG. 2B is a cross-sectional view of FIG. 2A taken along lines A-B and C-D. This light-emitting device includes a driver circuit portion (source line driver circuit) 601, a pixel portion 602, and a driver circuit portion (gate line driver circuit) 603, which can control light emission of a light-emitting element and illustrated with dotted lines. A reference numeral 604 denotes a sealing substrate; 605, a sealing material; and 607, a space surrounded by the sealing material 605.

Reference numeral 608 denotes a wiring for transmitting signals to be input to the source line driver circuit 601 and the gate line driver circuit 603 and receiving signals such as a video signal, a clock signal, a start signal, and a reset signal from a flexible printed circuit (FPC) 609 serving as an external input terminal. Although only the FPC is illustrated here, a printed wiring board (PWB) may be attached to the FPC. The light-emitting device in the present specification includes, in its category, not only the light-emitting device itself but also the light-emitting device provided with the FPC or the PWB.

Next, a cross-sectional structure will be described with reference to FIG. 2B. The driver circuit portion and the pixel portion are formed over an element substrate 610; the source line driver circuit 601, which is a driver circuit portion, and one of the pixels in the pixel portion 602 are illustrated here.

As the source line driver circuit 601, a CMOS circuit in which an n-channel FET 623 and a p-channel FET 624 are combined is formed. In addition, the driver circuit may be formed with any of a variety of circuits such as a CMOS circuit, a PMOS circuit, or an NMOS circuit. Although a driver integrated type in which the driver circuit is formed over the substrate is described in this embodiment, the driver circuit is not necessarily formed over the substrate, and the driver circuit can be formed outside, not over the substrate.

The pixel portion 602 includes a plurality of pixels including a switching FET 611, a current controlling FET 612, and a first electrode 613 electrically connected to a drain of the current controlling FET 612. One embodiment of the present invention is not limited to the structure. The pixel portion may include three or more FETs and a capacitor in combination.

The kind and crystallinity of a semiconductor used for the FETs is not particularly limited; an amorphous semiconductor or a crystalline semiconductor may be used. Examples of the semiconductor used for the FETs include Group 13 semiconductors, Group 14 semiconductors, compound semiconductors, oxide semiconductors, and organic semiconductor materials. Oxide semiconductors are particularly preferable. Examples of the oxide semiconductor include an In—Ga oxide and an In-M-Zn oxide (M is Al, Ga, Y, Zr, La, Ce, or Nd). Note that an oxide semiconductor material that has an energy gap of 2 eV or more, preferably 2.5 eV or more, further preferably 3 eV or more is preferably used, in which case the off-state current of the transistors can be reduced.

Note that to cover an end portion of the first electrode 613, an insulator 614 is formed. The insulator 614 can be formed using a positive photosensitive acrylic resin film here.

The insulator 614 is formed to have a curved surface with curvature at its upper or lower end portion in order to obtain favorable coverage. For example, in the case where positive photosensitive acrylic is used for a material of the insulator 614, only the upper end portion of the insulator 614 preferably has a curved surface with a curvature radius (0.2 μm to 3 μm). As the insulator 614, either a negative photosensitive resin or a positive photosensitive resin can be used.

An EL layer 616 and a second electrode 617 are formed over the first electrode 613. The first electrode 613, the EL layer 616, and the second electrode 617 correspond, respectively, to the first electrode 101, the EL layer 103, and the second electrode 102 in FIG. 1A or 1B.

The EL layer 616 preferably contains the organometallic complex of one embodiment of the present invention. The organometallic complex is preferably used as an emission center substance in the light-emitting layer.

The sealing substrate 604 is attached to the element substrate 610 with the sealing material 605, so that a light-emitting element 618 is provided in the space 607 surrounded by the element substrate 610, the sealing substrate 604, and the sealing material 605. The space 607 is filled with a filler, and may be filled with an inert gas (such as nitrogen or argon) or the sealing material 605. It is preferable that the sealing substrate 604 be provided with a recessed portion and a drying agent be provided in the recessed portion, in which case deterioration due to influence of moisture can be suppressed.

An epoxy-based resin or glass frit is preferably used for the sealing material 605. It is preferable that such a material do not transmit moisture or oxygen as much as possible. As the element substrate 610 and the sealing substrate 604, a glass substrate, a quartz substrate, or a plastic substrate formed of fiber reinforced plastic (FRP), polyvinyl fluoride (PVF), polyester, or acrylic can be used.

Note that in this specification and the like, a transistor or a light-emitting element can be formed using any of a variety of substrates, for example. The type of a substrate is not limited to a certain type. As the substrate, a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, a base material film, or the like can be used, for example. As an example of a glass substrate, a barium borosilicate glass substrate, an aluminoborosilicate glass substrate, a soda lime glass substrate, or the like can be given. Examples of the flexible substrate, the attachment film, the base material film, and the like are substrates of plastics typified by polyethylene terephthalate (PET), polyethylene naphthalate (PEN), and polyether sulfone (PES). Another example is a synthetic resin such as acrylic. Alternatively, polytetrafluoroethylene (PTFE), polypropylene, polyester, polyvinyl fluoride, polyvinyl chloride, or the like can be used. Alternatively, polyamide, polyimide, aramid, epoxy, an inorganic vapor deposition film, paper, or the like can be used. Specifically, the use of semiconductor substrates, single crystal substrates, SOI substrates, or the like enables the manufacture of small-sized transistors with a small variation in characteristics, size, shape, or the like and with high current capability. A circuit using such transistors achieves lower power consumption of the circuit or higher integration of the circuit.

Alternatively, a flexible substrate may be used as the substrate, and the transistor or the light-emitting element may be provided directly on the flexible substrate. Still alternatively, a separation layer may be provided between the substrate and the transistor or the substrate and the light-emitting element. The separation layer can be used when part or the whole of a semiconductor device formed over the separation layer is separated from the substrate and transferred onto another substrate. In such a case, the transistor can be transferred to a substrate having low heat resistance or a flexible substrate. For the separation layer, a stack including inorganic films, which are a tungsten film and a silicon oxide film, or an organic resin film of polyimide or the like formed over a substrate can be used, for example.

In other words, a transistor or a light-emitting element may be formed using one substrate, and then transferred to another substrate. Examples of a substrate to which a transistor or a light-emitting element is transferred include, in addition to the above-described substrates over which transistors can be formed, a paper substrate, a cellophane substrate, an aramid film substrate, a polyimide film substrate, a stone substrate, a wood substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, and a rubber substrate. When such a substrate is used, a transistor with excellent characteristics or a transistor with low power consumption can be formed, a device with high durability or high heat resistance can be provided, or reduction in weight or thickness can be achieved.

FIGS. 3A and 3B each illustrate an example of a light-emitting device in which full color display is achieved by formation of a light-emitting element exhibiting white light emission and with the use of coloring layers (color filters) and the like. In FIG. 3A, a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting elements, a partition 1025, an EL layer 1028, a second electrode 1029 of the light-emitting elements, a sealing substrate 1031, a sealing material 1032, and the like are illustrated.

In FIG. 3A, coloring layers (a red coloring layer 1034R, a green coloring layer 1034G, and a blue coloring layer 1034B) are provided on a transparent base material 1033. A black layer (a black matrix) 1035 may be additionally provided. The transparent base material 1033 provided with the coloring layers and the black layer is positioned and fixed to the substrate 1001. Note that the coloring layers and the black layer are covered with an overcoat layer 1036. In FIG. 3A, light emitted from part of the light-emitting layer does not pass through the coloring layers, while light emitted from the other part of the light-emitting layer passes through the coloring layers. Since light which does not pass through the coloring layers is white and light which passes through any one of the coloring layers is red, blue, or green, an image can be displayed using pixels of the four colors.

Note that a light-emitting element including the organometallic complex of one embodiment of the present invention as a light-emitting substance can have high emission efficiency and low power consumption.

FIG. 3B illustrates an example in which the coloring layers (the red coloring layer 1034R, the green coloring layer 1034G, and the blue coloring layer 1034B) are provided between the gate insulating film 1003 and the first interlayer insulating film 1020. As in the structure, the coloring layers may be provided between the substrate 1001 and the sealing substrate 1031.

Figure 4:
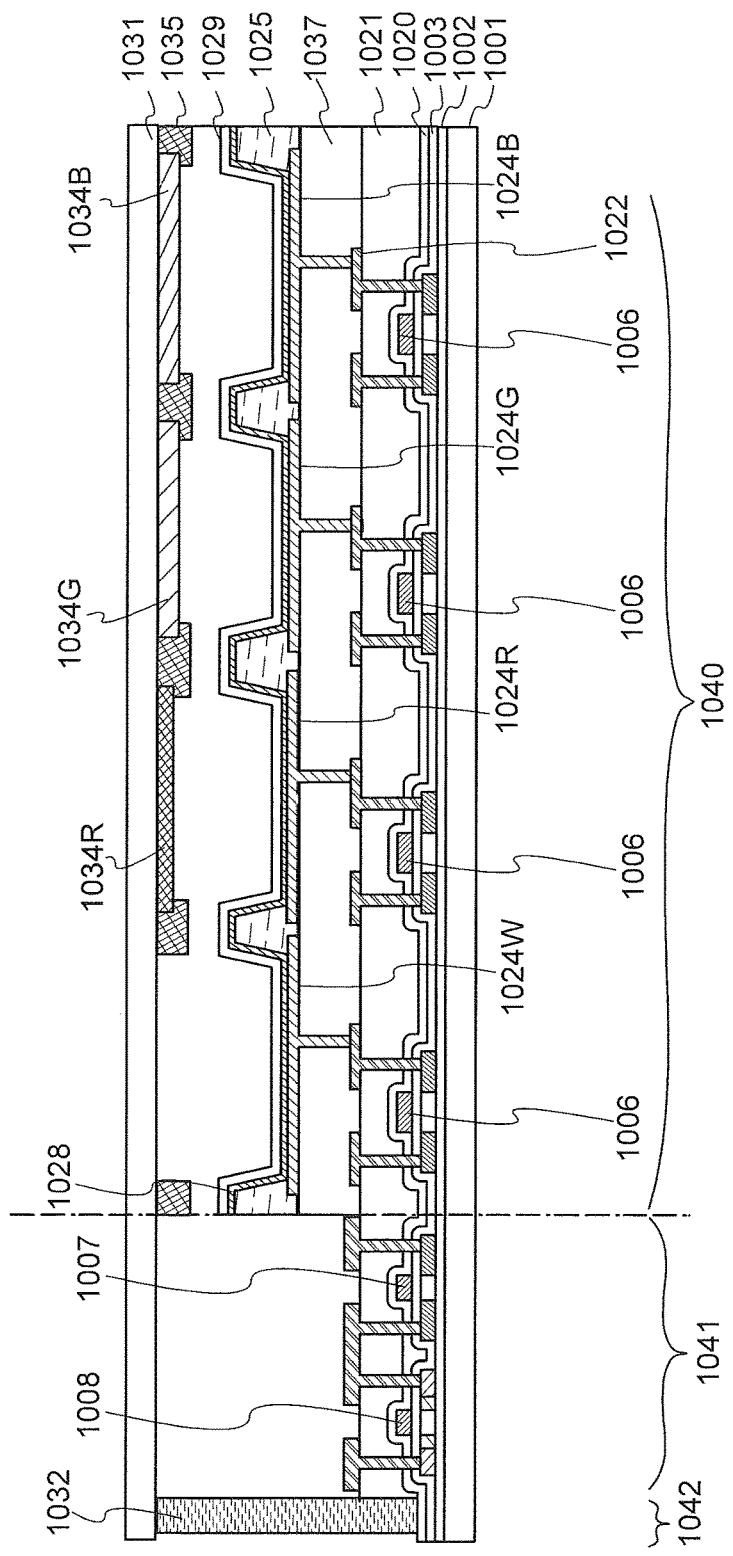
FIG. 4 is a conceptual diagram of an active matrix light-emitting device.

The above-described light-emitting device is a light-emitting device having a structure in which light is extracted from the substrate 1001 side where the FETs are formed (a bottom emission structure), but may be a light-emitting device having a structure in which light is extracted from the sealing substrate 1031 side (a top emission structure). FIG. 4 is a cross-sectional view of a light-emitting device having a top emission structure. In this case, a substrate which does not transmit light can be used as the substrate 1001. The process up to the step of forming a connection electrode which connects the FET and the anode of the light-emitting element is performed in a manner similar to that of the light-emitting device having a bottom emission structure. Then, a third interlayer insulating film 1037 is formed to cover an electrode 1022. This insulating film may have a planarization function. The third interlayer insulating film 1037 can be formed using a material similar to that of the second interlayer insulating film, and can alternatively be formed using any of other various materials.

The first electrodes 1024W, 1024R, 1024G, and 1024B of the light-emitting elements each serve as an anode here, but may serve as a cathode. Furthermore, in the case of a light-emitting device having a top emission structure as illustrated in FIG. 4, the first electrodes are preferably reflective electrodes. The EL layer 1028 is formed to have a structure similar to the structure of the EL layer 103 in FIG. 1A or 1B, with which white light emission can be obtained.

In the case of a top emission structure as illustrated in FIG. 4, sealing can be performed with the sealing substrate 1031 on which the coloring layers (the red coloring layer 1034R, the green coloring layer 1034G, and the blue coloring layer 1034B) are provided. The sealing substrate 1031 may be provided with the black layer (black matrix) 1035 which is positioned between pixels. The coloring layers (the red coloring layer 1034R, the green coloring layer 1034G, and the blue coloring layer 1034B) and the black layer (the black matrix) may be covered with the overcoat layer. Note that a light-transmitting substrate is used as the sealing substrate 1031.

Although an example in which full color display is performed using four colors of red, green, blue, and white is shown here, there is no particular limitation and full color display using three colors of red, green, and blue or four colors of red, green, blue, and yellow may be performed.

Figure 5A:
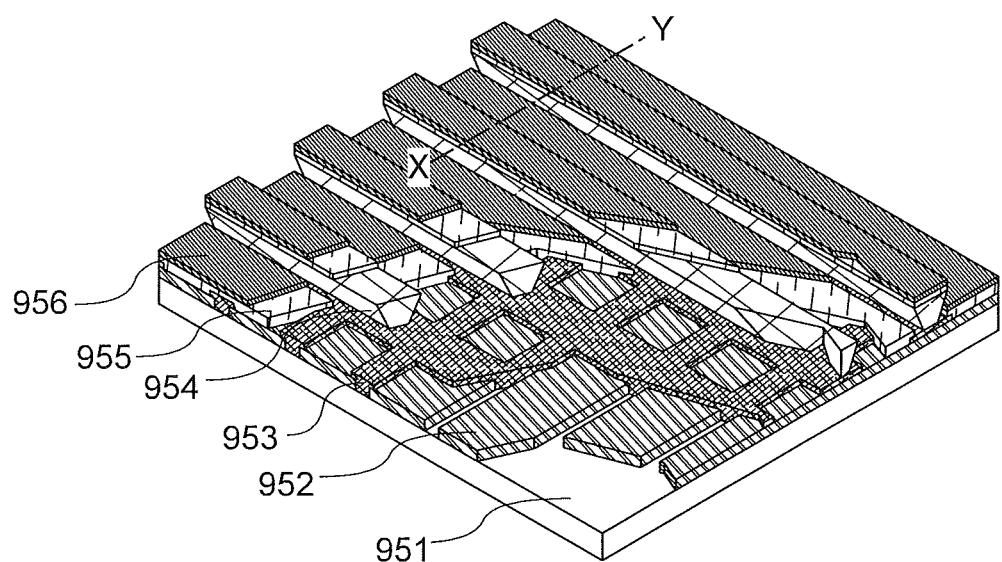
FIGS. 5A and 5B are conceptual diagrams of a passive matrix light-emitting device.
Figure 5B:
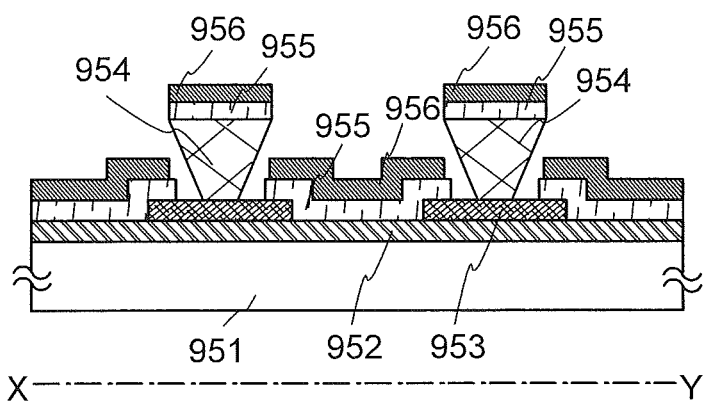

FIGS. 5A and 5B illustrate a passive matrix light-emitting device which is one embodiment of the present invention. FIG. 5A is a perspective view of the light-emitting device, and FIG. 5B is a cross-sectional view of FIG. 5A taken along line X-Y. In FIGS. 5A and 5B, an EL layer 955 is provided between an electrode 952 and an electrode 956 over a substrate 951. An end portion of the electrode 952 is covered with an insulating layer 953. A partition layer 954 is provided over the insulating layer 953. The sidewalls of the partition layer 954 are aslope such that the distance between both sidewalls is gradually narrowed toward the surface of the substrate. In other words, a cross section taken along the direction of the short side of the partition layer 954 is trapezoidal, and the lower side (a side which is in the same direction as a plane direction of the insulating layer 953 and in contact with the insulating layer 953) is shorter than the upper side (a side which is in the same direction as the plane direction of the insulating layer 953 and not in contact with the insulating layer 953). The partition layer 954 thus provided can prevent defects in the light-emitting element due to static electricity or the like.

Since many minute light-emitting elements arranged in a matrix can each be controlled with the FETs formed in the pixel portion, the above-described light-emitting device can be suitably used as a display device for displaying images.

<<Lighting Device>>

Figure 6A:
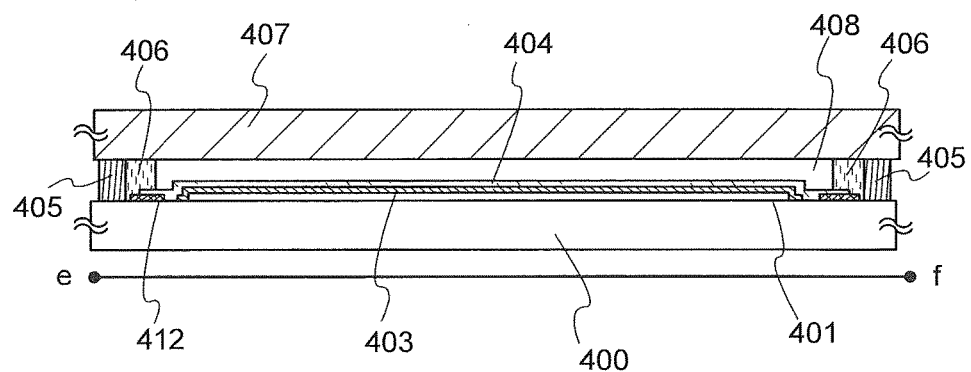
FIGS. 6A and 6B illustrate a lighting device.
Figure 6B:
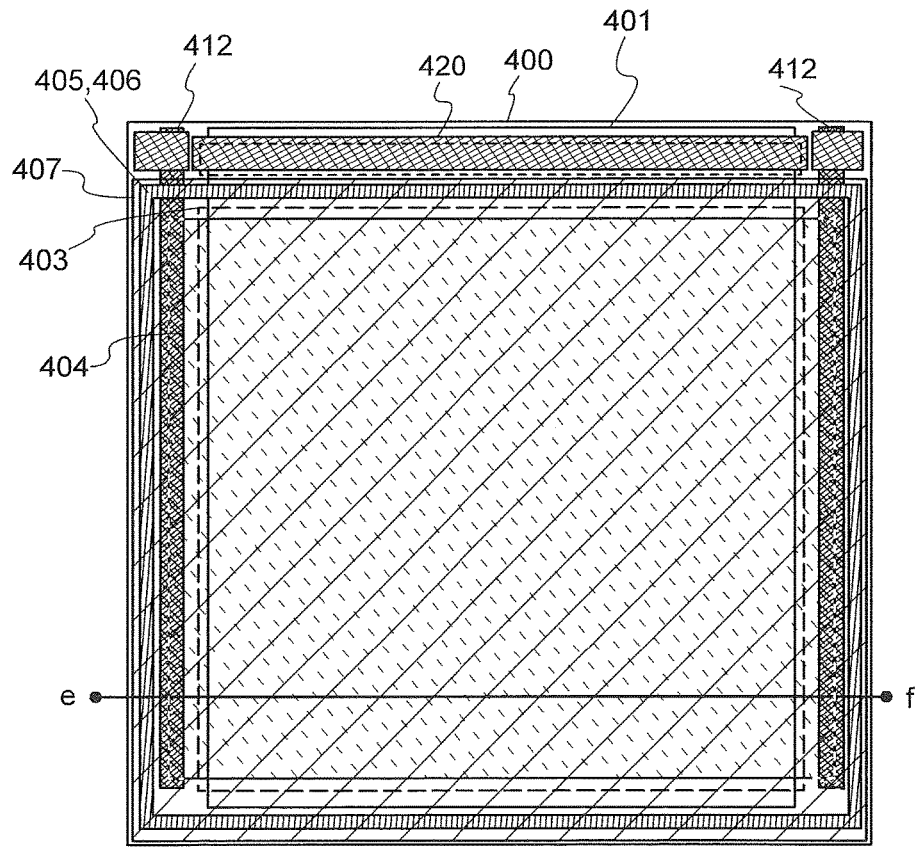

A lighting device which is one embodiment of the present invention is described with reference to FIGS. 6A and 6B. FIG. 6B is a top view of the lighting device, and FIG. 6A is a cross-sectional view of FIG. 6B taken along line e-f.

In the lighting device, a first electrode 401 is formed over a substrate 400 which is a support and has a light-transmitting property. The first electrode 401 corresponds to the first electrode 101 in FIGS. 1A and 1B. When light is extracted through the first electrode 401 side, the first electrode 401 is formed using a material having a light-transmitting property.

A pad 412 for applying a voltage to a second electrode 404 is provided over the substrate 400.

An EL layer 403 is formed over the first electrode 401. The EL layer 403 corresponds to, for example, the EL layer 103 in FIG. 1A or 1B. Refer to the descriptions for the structure.

The second electrode 404 is formed to cover the EL layer 403. The second electrode 404 corresponds to the second electrode 102 in FIG. 1A. The second electrode 404 contains a material having high reflectivity when light is extracted through the first electrode 401 side. The second electrode 404 is connected to the pad 412, whereby a voltage is applied.

A light-emitting element is formed with the first electrode 401, the EL layer 403, and the second electrode 404. The light-emitting element is fixed to a sealing substrate 407 with sealing materials 405 and 406 and sealing is performed, whereby the lighting device is completed. It is possible to use only either the sealing material 405 or the sealing material 406. In addition, the inner sealing material 406 (not shown in FIG. 6B) can be mixed with a desiccant, whereby moisture is adsorbed and the reliability is increased.

When parts of the pad 412 and the first electrode 401 are extended to the outside of the sealing materials 405 and 406, the extended parts can serve as external input terminals. An IC chip 420 mounted with a converter or the like may be provided over the external input terminals.

<<Electronic Device>>

Examples of an electronic device which is one embodiment of the present invention are described. Examples of the electronic device are television devices (also referred to as TV or television receivers), monitors for computers and the like, cameras such as digital cameras and digital video cameras, digital photo frames, mobile phones (also referred to as cell phones or mobile phone devices), portable game machines, portable information terminals, audio playback devices, and large game machines such as pachinko machines. Specific examples of these electronic devices are given below.

FIG. 7A illustrates an example of a television device. In the television device, a display portion 7103 is incorporated in a housing 7101. In addition, here, the housing 7101 is supported by a stand 7105. Images can be displayed on the display portion 7103, and in the display portion 7103, light-emitting elements are arranged in a matrix.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the use of the receiver, general television broadcasting can be received. Moreover, when the television device is connected to a communication network with or without wires via the modem, one-way (from a sender to a receiver) or two-way (between a sender and a receiver or between receivers) information communication can be performed.

FIG. 7B1 illustrates a computer, which includes a main body 7201, a housing 7202, a display portion 7203, a keyboard 7204, an external connection port 7205, a pointing device 7206, and the like. Note that this computer is manufactured by using light-emitting elements arranged in a matrix in the display portion 7203. The computer illustrated in FIG. 7B1 may have a structure illustrated in FIG. 7B2. A computer illustrated in FIG. 7B2 is provided with a second display portion 7210 instead of the keyboard 7204 and the pointing device 7206. The second display portion 7210 is a touchscreen, and input can be performed by operation of display for input on the second display portion 7210 with a finger or a dedicated pen. The second display portion 7210 can also display images other than the display for input. The display portion 7203 may also be a touchscreen. Connecting the two screens with a hinge can prevent troubles; for example, the screens can be prevented from being cracked or broken while the computer is being stored or carried.

FIGS. 7C and 7D illustrate an example of a portable information terminal. The portable information terminal is provided with a display portion 7402 incorporated in a housing 7401, operation buttons 7403, an external connection port 7404, a speaker 7405, a microphone 7406, and the like. Note that the portable information terminal has the display portion 7402 including light-emitting elements arranged in a matrix.

Information can be input to the portable information terminal illustrated in FIGS. 7C and 7D by touching the display portion 7402 with a finger or the like. In this case, operations such as making a call and creating an e-mail can be performed by touching the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are combined.

For example, in the case of making a call or creating an e-mail, a text input mode mainly for inputting text is selected for the display portion 7402 so that text displayed on a screen can be input. In this case, it is preferable to display a keyboard or number buttons on almost the entire screen of the display portion 7402.

When a detection device including a sensor such as a gyroscope or an acceleration sensor for sensing inclination is provided inside the mobile phone, screen display of the display portion 7402 can be automatically changed by determining the orientation of the mobile phone (whether the mobile phone is placed horizontally or vertically).

The screen modes are switched by touch on the display portion 7402 or operation with the operation buttons 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken by the display portion 7402 while in touch with the palm or the finger, whereby personal authentication can be performed. Furthermore, by providing a backlight or a sensing light source which emits near-infrared light in the display portion, an image of a finger vein, a palm vein, or the like can be taken.

Note that in the above electronic devices, any of the structures described in this specification can be combined as appropriate.

The display portion preferably includes a light-emitting element including the organometallic complex of one embodiment of the present invention. The light-emitting element can have high emission efficiency. Furthermore, the light-emitting element can be driven at low voltage. Thus, the electronic device including the organometallic complex of one embodiment of the present invention can have low power consumption.

Figure 8:
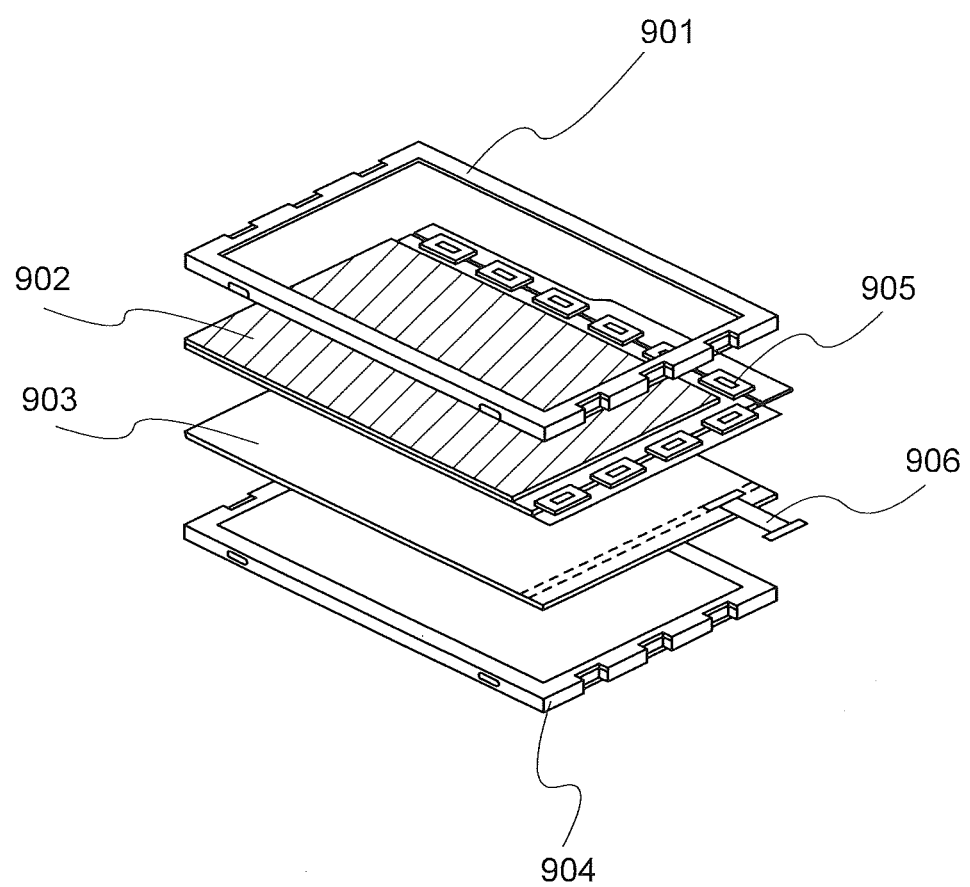
FIG. 8 illustrates a light source device.

FIG. 8 illustrates an example of a liquid crystal display device including the light-emitting element for a backlight. The liquid crystal display device illustrated in FIG. 8 includes a housing 901, a liquid crystal layer 902, a backlight unit 903, and a housing 904. The liquid crystal layer 902 is connected to a driver IC 905. The light-emitting element is used for the backlight unit 903, to which current is supplied through a terminal 906.

As the light-emitting element, a light-emitting element including the organometallic complex of one embodiment of the present invention is preferably used. By including the light-emitting element, the backlight of the liquid crystal display device can have low power consumption.

Figure 9:
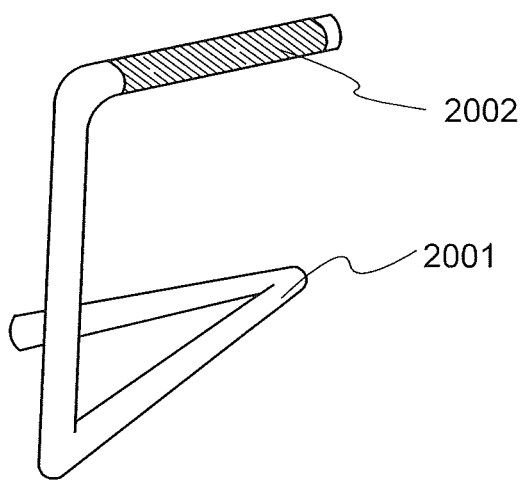
FIG. 9 illustrates a lighting device.

FIG. 9 illustrates an example of a desk lamp which is one embodiment of the present invention. The desk lamp illustrated in FIG. 9 includes a housing 2001 and a light source 2002, and a lighting device including a light-emitting element is used as the light source 2002.

Figure 10:
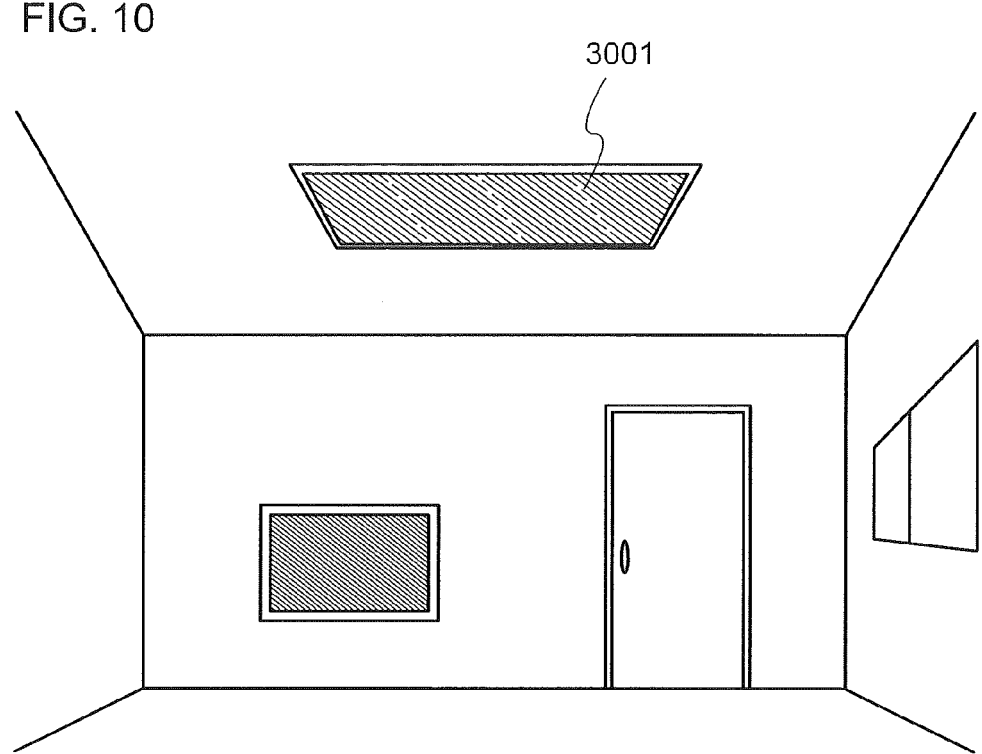
FIG. 10 illustrates a lighting device.

FIG. 10 illustrates an example of an indoor lighting device 3001. A light-emitting element including the organometallic complex of one embodiment of the present invention is preferably used in the lighting device 3001.

Figure 11:
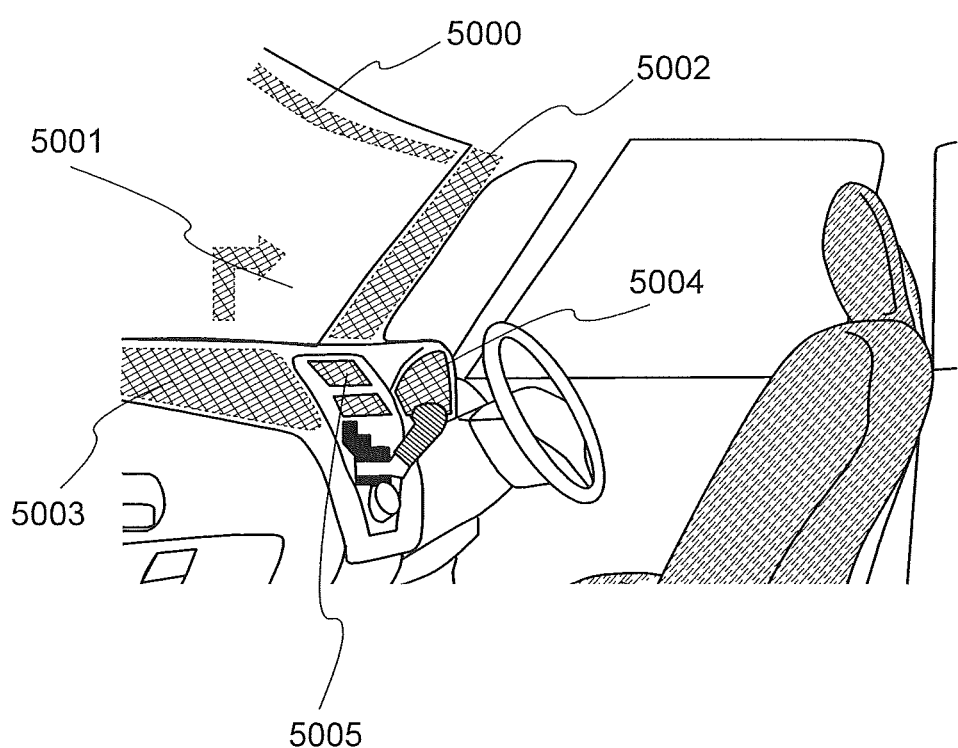
FIG. 11 illustrates in-vehicle display devices and lighting devices.

An automobile which is one embodiment of the present invention is illustrated in FIG. 11. In the automobile, light-emitting elements are used for a windshield and a dashboard. Display regions 5000 to 5005 are provided by using the light-emitting elements. The light-emitting elements preferably include the organometallic complex of one embodiment of the present invention, in which case the light-emitting elements can have low power consumption. This also suppresses power consumption of the display regions 5000 to 5005, showing suitability for use in an automobile.

The display regions 5000 and 5001 are display devices which are provided in the automobile windshield and which include the light-emitting elements. When a first electrode and a second electrode are formed of electrodes having light-transmitting properties in these light-emitting elements, what is called a see-through display device, through which the opposite side can be seen, can be obtained. Such a see-through display device can be provided even in the automobile windshield, without hindering the vision. Note that in the case where a transistor for driving or the like is provided, a transistor having a light-transmitting property, such as an organic transistor using an organic semiconductor material or a transistor using an oxide semiconductor, is preferably used.

The display region 5002 is a display device which is provided in a pillar portion and which includes the light-emitting element. The display region 5002 can compensate for the view hindered by the pillar portion by showing an image taken by an imaging unit provided in the car body. Similarly, a display region 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see makes it possible for the driver to confirm safety easily and comfortably.

The display region 5004 and the display region 5005 can provide a variety of kinds of information such as navigation information, a speedometer, a tachometer, a mileage, a fuel meter, a gearshift indicator, and air-condition setting. The content or layout of the display can be changed freely by a user as appropriate. Note that such information can also be shown by the display regions 5000 to 5003. The display regions 5000 to 5005 can also be used as lighting devices.

Figure 12A:
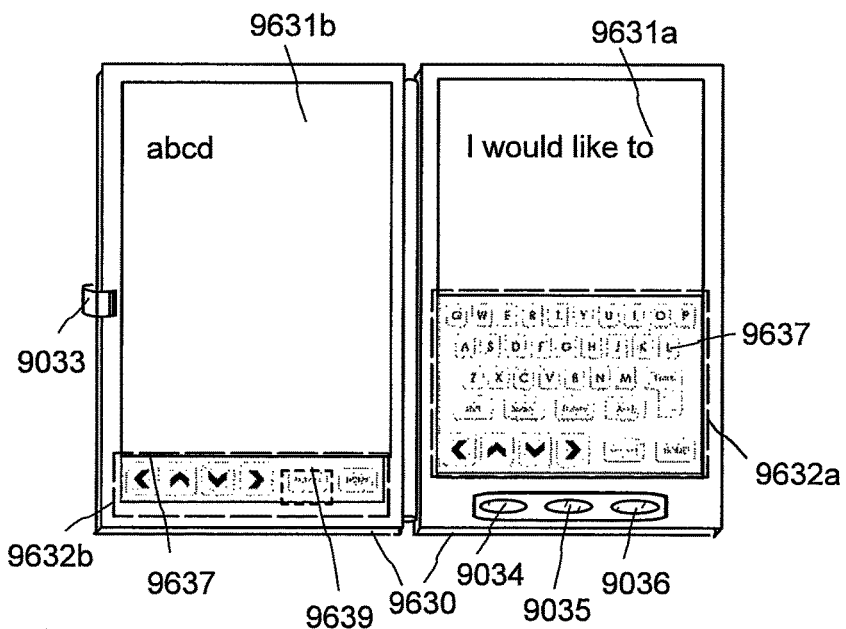
FIGS. 12A to 12C illustrate an electronic device.
Figure 12B:
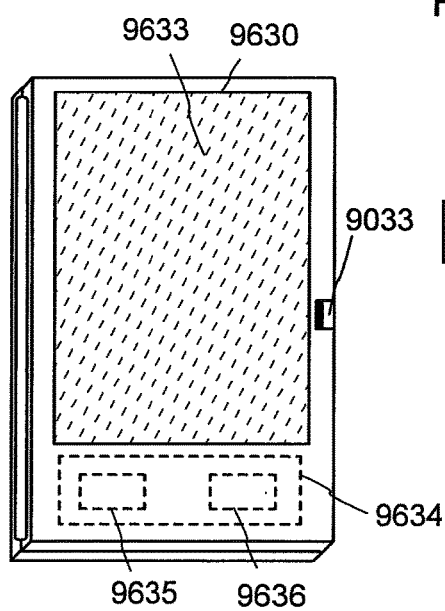

FIGS. 12A and 12B illustrate an example of a foldable tablet terminal. FIG. 12A illustrates the tablet terminal which is unfolded. The tablet terminal includes a housing 9630, a display portion 9631a, a display portion 9631b, a display mode switch 9034, a power switch 9035, a power-saving mode switch 9036, a clip 9033, and an operation switch 9038. Note that in the tablet terminal, one or both of the display portion 9631a and the display portion 9631b is/are formed using a light-emitting device which includes the light-emitting element containing the organometallic complex of one embodiment of the present invention.

Part of the display portion 9631a can be a touchscreen region 9632a and data can be input when a displayed operation key 9637 is touched. Although half of the display portion 9631a has only a display function and the other half has a touchscreen function, one embodiment of the present invention is not limited to the structure. The whole display portion 9631a may have a touchscreen function. For example, a keyboard can be displayed on the entire region of the display portion 9631a so that the display portion 9631a is used as a touchscreen, and the display portion 9631b can be used as a display screen.

Like the display portion 9631a, part of the display portion 9631b can be a touchscreen region 9632b. When a switching button 9639 for showing/hiding a keyboard on the touchscreen is touched with a finger, a stylus, or the like, the keyboard can be displayed on the display portion 9631b.

Touch input can be performed in the touchscreen region 9632a and the touchscreen region 9632b at the same time.

The display mode switch 9034 can switch the display between portrait mode, landscape mode, and the like, and between monochrome display and color display, for example. The power-saving mode switch 9036 can control display luminance in accordance with the amount of external light in use of the tablet terminal sensed by an optical sensor incorporated in the tablet terminal. Another sensing device including a sensor such as a gyroscope or an acceleration sensor for sensing inclination may be incorporated in the tablet terminal, in addition to the optical sensor.

Although FIG. 12A illustrates an example in which the display portion 9631a and the display portion 9631b have the same display area, one embodiment of the present invention is not limited to the example. The display portion 9631a and the display portion 9631b may have different display areas and different display quality. For example, higher resolution images may be displayed on one of the display portions 9631a and 9631b.

FIG. 12B illustrates the tablet terminal which is folded. The tablet terminal in this embodiment includes the housing 9630, a solar cell 9633, a charge and discharge control circuit 9634, a battery 9635, and a DCDC converter 9636. In FIG. 12B, a structure including the battery 9635 and the DCDC converter 9636 is illustrated as an example of the charge and discharge control circuit 9634.

Since the tablet terminal is foldable, the housing 9630 can be closed when the tablet terminal is not in use. As a result, the display portion 9631a and the display portion 9631b can be protected, thereby providing a tablet terminal with high endurance and high reliability for long-term use.

The tablet terminal illustrated in FIGS. 12A and 12B can have other functions such as a function of displaying various kinds of data (e.g., a still image, a moving image, and a text image), a function of displaying a calendar, a date, the time, or the like on the display portion, a touch-input function of operating or editing the data displayed on the display portion by touch input, and a function of controlling processing by various kinds of software (programs).

The solar cell 9633 provided on a surface of the tablet terminal can supply power to the touchscreen, the display portion, a video signal processing portion, or the like. Note that a structure in which the solar cell 9633 is provided on one or both surfaces of the housing 9630 is preferable because the battery 9635 can be charged efficiently.

Figure 12C:
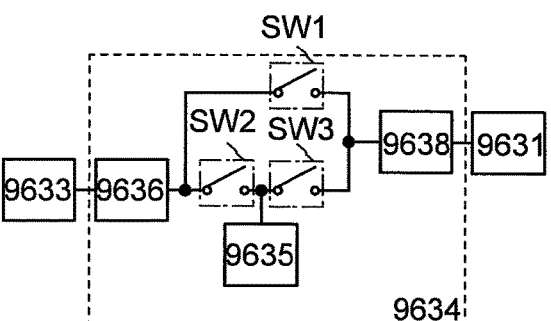

The structure and operation of the charge and discharge control circuit 9634 illustrated in FIG. 12B are described with reference to a block diagram of FIG. 12C. FIG. 12C illustrates the solar cell 9633, the battery 9635, the DCDC converter 9636, a converter 9638, switches SW1 to SW3, and a display portion 9631. The battery 9635, the DCDC converter 9636, the converter 9638, and the switches SW1 to SW3 correspond to the charge and discharge control circuit 9634 illustrated in FIG. 12B.

First, description is made on an example of the operation in the case where power is generated by the solar cell 9633 with the use of external light. The voltage of the power generated by the solar cell is raised or lowered by the DCDC converter 9636 so as to be voltage for charging the battery 9635. Then, when power from the solar cell 9633 is used for the operation of the display portion 9631, the switch SW1 is turned on and the voltage of the power is raised or lowered by the converter 9638 so as to be voltage needed for the display portion 9631. When images are not displayed on the display portion 9631, the switch SW1 is turned off and the switch SW2 is turned on so that the battery 9635 is charged.

Although the solar cell 9633 is described as an example of a power generation unit, the power generation unit is not particularly limited, and the battery 9635 may be charged by another power generation unit such as a piezoelectric element or a thermoelectric conversion element (Peltier element). The battery 9635 may be charged by a non-contact power transmission module capable of performing charging by transmitting and receiving power wirelessly (without contact), or another charge unit used in combination, and the power generation unit is not necessarily provided.

Note that the organometallic complex of one embodiment of the present invention can be used for an organic thin-film solar cell. Specifically, the organometallic complex can be used in a carrier-transport layer since the organometallic complex has a carrier-transport property. The organometallic complex can be photoexcited and hence can be used in a power generation layer.

One embodiment of the present invention is not limited to the tablet terminal having the shape illustrated in FIGS. 12A to 12C as long as the display portion 9631 is included.

Figure 13A:
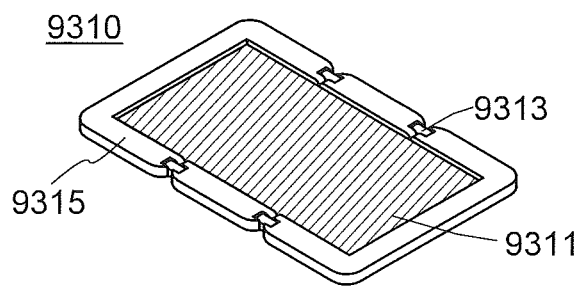
FIGS. 13A to 13C illustrate an electronic device.
Figure 13B:
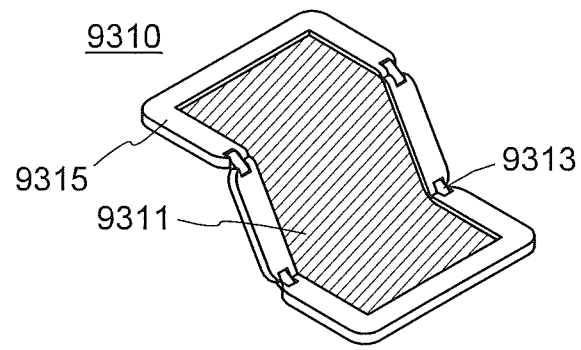
Figure 13C:
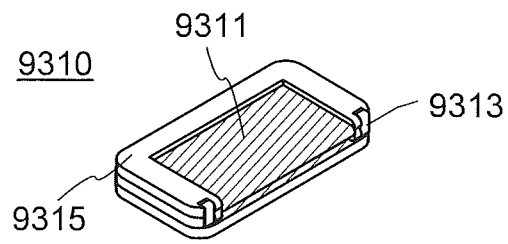

FIGS. 13A to 13C illustrate a foldable portable information terminal 9310. FIG. 13A illustrates the portable information terminal 9310 that is opened. FIG. 13B illustrates the portable information terminal 9310 that is being opened or being folded. FIG. 13C illustrates the portable information terminal 9310 that is folded. The portable information terminal 9310 is highly portable when folded. When the portable information terminal 9310 is opened, a seamless large display region is highly browsable.

A display panel 9311 is supported by three housings 9315 joined together by hinges 9313. Note that the display panel 9311 may be a touch panel (an input/output device) including a touch sensor (an input device). By bending the display panel 9311 at a connection portion between two housings 9315 with the use of the hinges 9313, the portable information terminal 9310 can be reversibly changed in shape from an opened state to a folded state. The light-emitting device of one embodiment of the present invention can be used for the display panel 9311. A display region 9312 in the display panel 9311 is a display region that is positioned at the side surface of the portable information terminal 9310 that is folded. On the display region 9312, information icons, file shortcuts of frequently used applications or programs, and the like can be displayed, and confirmation of information and start of application can be smoothly performed.

Example 1

Synthesis Example 1

In this synthesis example, a synthesis example of {2-[6-(3,5-dimethyl-pyrazol-1-yl-$\kappa N^2$)-1,2-phenylene-$\kappa C^1$]oxy[10-(2-pyridinyl-$\kappa N$)-phenothiazine-2,1-diyl-$\kappa C^1$]}platinum(II) (abbreviation: [Pt(pptOppz)]), which is the organometallic complex of one embodiment of the present invention and represented by the structural formula (100) in Embodiment, is specifically described. A structural formula of [Pt(pptOppz)] is shown below.

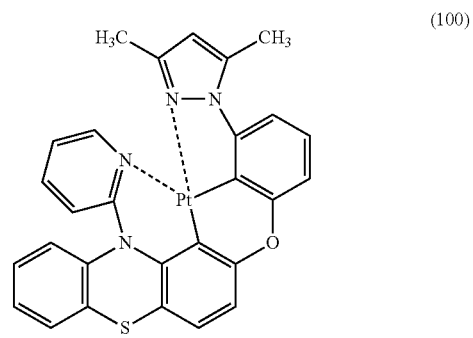

Step 1: Synthesis of
2-methoxy-10-(pyridin-2-yl)-phenothiazine

First, 3.1 g of 2-methoxy phenothiazine, 3.1 g of 2-iodopyridine, and 2.0 g of sodium-t-butoxide were put into a three-neck flask equipped with a reflux pipe, and the air in the flask was replaced with nitrogen. Then, 97 mL of toluene, 0.56 g of 2-dicyclohexylphosphino-2',6'-dimethoxybiphenyl (product name: SPhos), and 0.62 g of tris(dibenzylideneacetone)dipalladium(0) (abbreviation: Pd$_2$(dba)$_3$) were added to this mixture, and the mixture was heated and stirred at 130° C. for 14 hours. Water was added to the obtained mixture, and an organic layer was extracted with ethyl acetate. The solution of the extract was washed with saturated brine. Then, magnesium sulfate was added and filtration was performed. The solvent of the filtrate was distilled off and the obtained residue was purified by flash column chromatography using ethyl acetate and hexane in a ratio of 1:5 as a developing solvent, so that the desired substance was obtained as 2.2 g of a brown oily substance in a yield of 52%. The synthesis scheme of the step 1 is illustrated in the following equation (1-1).

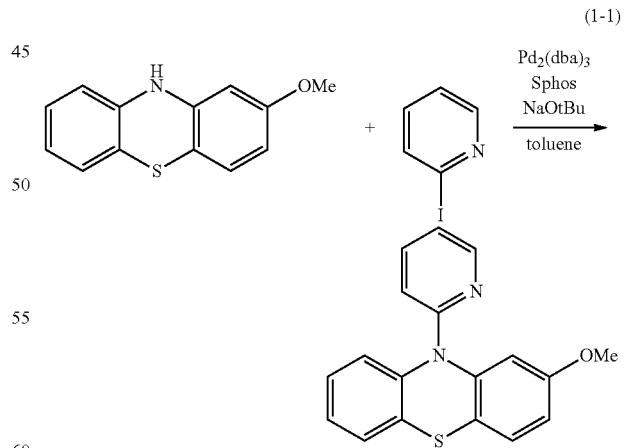

Step 2: Synthesis of
2-hydroxy-10-(pyridin-2-yl)-phenothiazine

Next, 7.1 g of 2-methoxy-10-(pyridin-2-yl)-phenothiazine and 13 g of pyridine hydrochloride were put into a three-neck flask equipped with a reflux pipe, and the air in the flask was replaced with nitrogen. The mixture was heated and stirred at 170° C. for 7 hours. Furthermore, 2 g of pyridine hydrochloride was added, and the mixture was heated and stirred at 170° C. for 6 hours. The temperature of the flask was reduced to 90° C., ethyl acetate and water were added, and the mixture was stirred for 30 minutes. An organic layer of the obtained mixture solution was extracted with ethyl acetate. The solution of the extract was washed with saturated brine. Then, magnesium sulfate was added and filtration was performed. The solvent of the filtrate was distilled off, a solution containing ethyl acetate and hexane in a ratio of 1:2 was added to the obtained residue, and filtration was performed. This residue was dissolved in ethyl acetate, and the mixture was filtered through a filter aid filled with Celite (produced by Wako Pure Chemical Industries, Ltd., Catalog No. 531-16855). The solvent of the filtrate was distilled off and recrystallization was performed with toluene, so that the desired substance was obtained as 3.0 g of a greenish gray solid in a yield of 45%. The synthesis scheme of the step 2 is illustrated in the following equation (1-2).

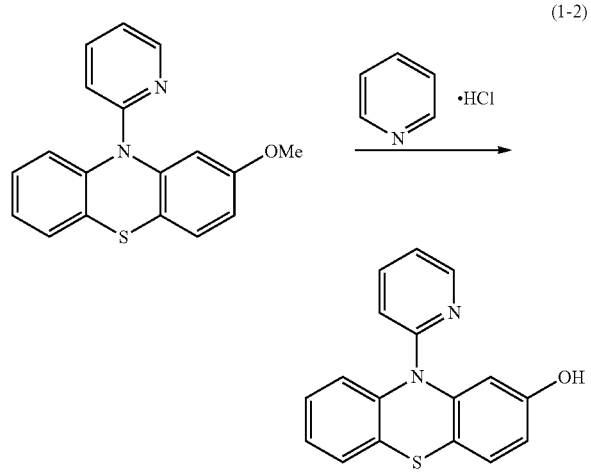

(1-2)

Step 3: Synthesis of 1-(3-iodophenyl)-3,5-dimethylpyrazol

Next, 5.0 g of 1,3-diiodobenzene, 1.6 g of 3,5-dimethylpyrazol, 220 mg of copper(I) oxide, 370 mg of pyridin-2-aldoxime, and 12 g of cesium carbonate were put into a three-neck flask equipped with a reflux pipe, and the air in the flask was replaced with nitrogen. Then, 300 mL of acetonitrile was added, and the mixture was refluxed for 37 hours. The obtained mixture was dissolved in dichloromethane, and the mixture was filtered through a filter aid filled with Celite. The solvent of the filtrate was distilled off and purification was performed by silica gel column chromatography using ethyl acetate and hexane in a ratio of 1:5 as a developing solvent, so that the desired substance was obtained as 3.0 g of a brown oily substance in a yield of 40%. The synthesis scheme of the step 3 is illustrated in the following equation (1-3).

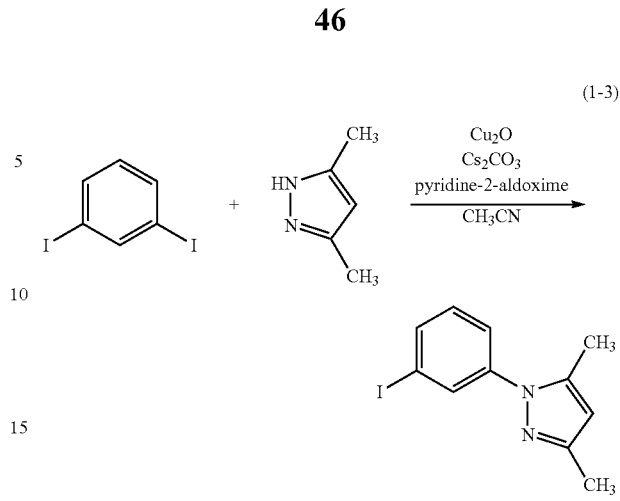

(1-3)

Step 4: Synthesis of 2-[3-(3,5-dimethylpyrazol-1-yl)phenoxy]-10-(pyridin-2-yl)-phenothiazine (abbreviation: HpptOppz)

Next, 1.0 g of 2-hydroxy-10-(pyridin-2-yl)-phenothiazine, 1.3 g of 1-(3-iodophenyl)-3,5-dimethylpyrazol, 1.1 g of picolinic acid, and 3.6 g of potassium phosphate were put into a three-neck flask equipped with a reflux pipe, and the air in the flask was replaced with nitrogen. Then, 100 mL of dimethyl sulfoxide and 0.33 g of copper iodide were added, and the mixture was heated at 150° C. for 14 hours. Furthermore, 1.1 g of picolinic acid, 3.6 g of potassium phosphate, and 0.33 g of copper iodide were added, and the mixture was heated at 150° C. for 15 hours. Water was added to the obtained mixture, and an organic layer was extracted with ethyl acetate. The solution of the extract was washed with saturated brine. Then, magnesium sulfate was added and filtration was performed. The solvent of the filtrate was distilled off and the obtained residue was purified by flash column chromatography using ethyl acetate and hexane in a ratio of 1:5 as a developing solvent, so that the desired substance was obtained as 1.3 g of a yellow solid in a yield of 82%. The synthesis scheme of the step 4 is illustrated in the following equation (1-4).

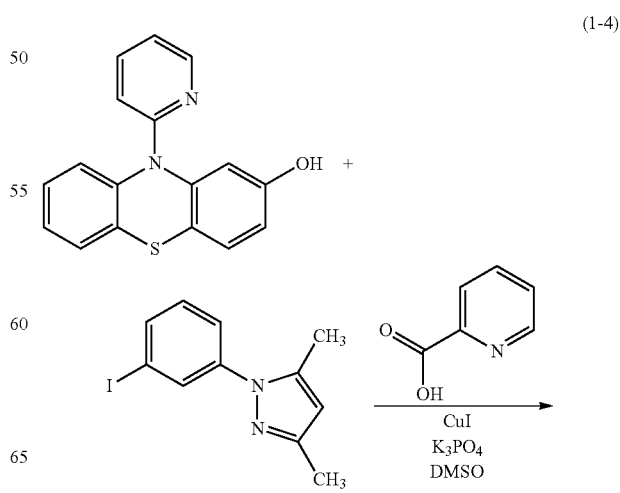

(1-4)

-continued

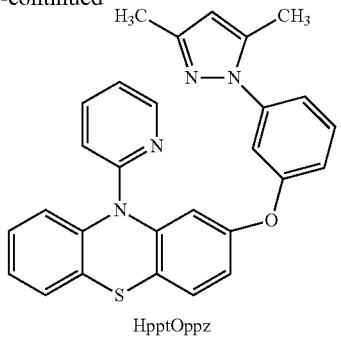

HpptOppz

Step 5: Synthesis of {2-[6-(3,5-dimethyl-pyrazol-1-yl-κN$^2$)-1,2-phenylene-κC$^1$]oxy[10-(2-pyridinyl-κN)-phenothiazine-2,1-diyl-κC$^1$]}platinum(II) (abbreviation: [Pt(pptOppz)])

Next, 1.3 g of HpptOppz, 1.3 g of potassium tetrachloroplatinate(II), and 40 mL of glacial acetic acid were added to the flask, the air in the flask was replaced with nitrogen, and the mixture was refluxed for 56 hours. Water was added to the obtained mixture, and the mixture was stirred for 20 minutes and filtered. This residue was purified by neutral silica gel column chromatography using dichloromethane and hexane in a ratio of 7:5 as a developing solvent. The solvent was distilled off from the obtained fraction of the desired substance and recrystallization was performed with a mixed solvent of chloroform, dichloromethane, methanol, and hexane to give 0.42 g of a yellowish white solid in a yield of 21%. The synthesis scheme of the step 5 is illustrated in the following equation (1-5).

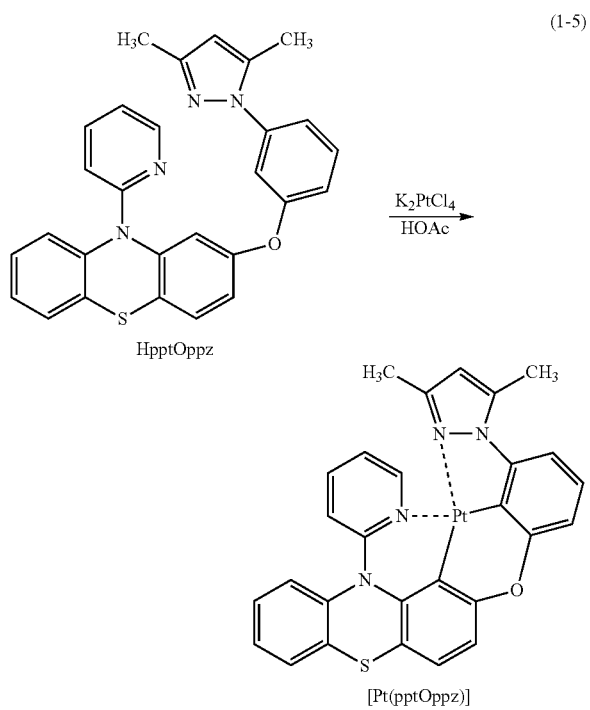

(1-5)

Figure 14A:
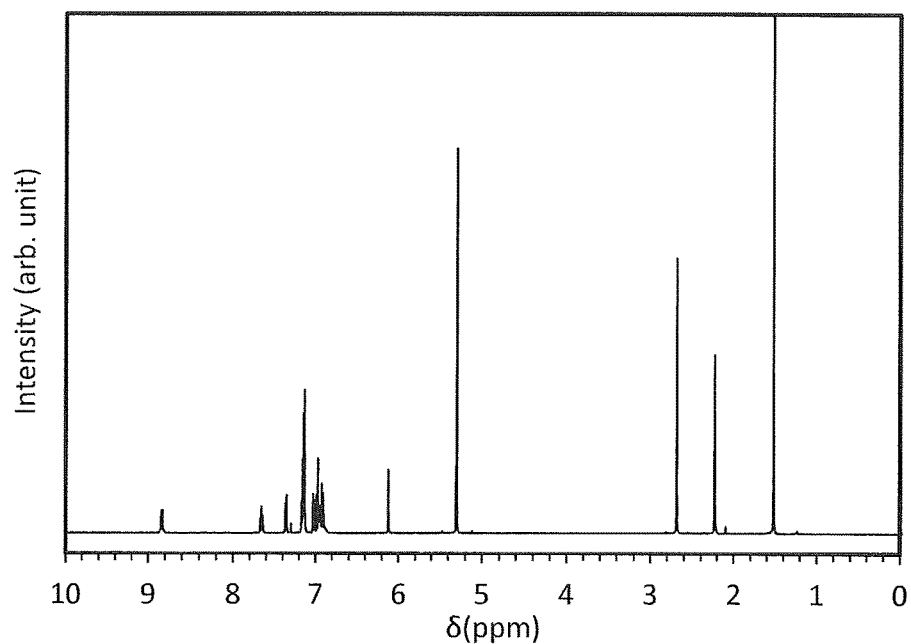
FIGS. 14A and 14B show NMR charts of [Pt(pptOppz)].
Figure 14B:
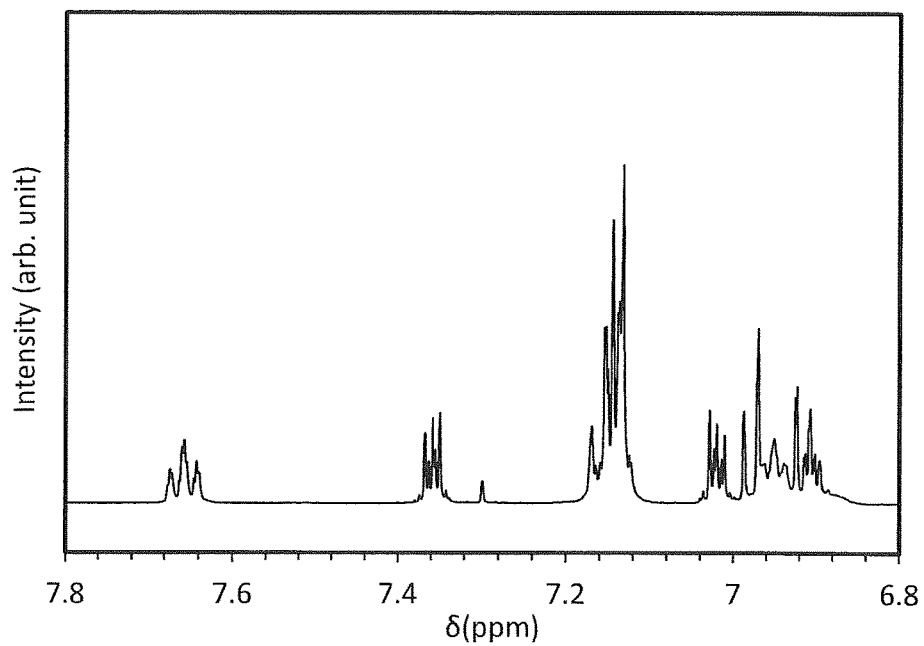

Analysis results by nuclear magnetic resonance ($^1$H-NMR) spectroscopy of the yellowish white solid obtained in the step 5 are described below. FIGS. 14A and 14B show the $^1$H-NMR charts. These results revealed that [Pt(pptOppz)], which is the organometallic complex of one embodiment of the present invention, was obtained.

$^1$H-NMR. δ(CDCl$_3$): 2.23 (s, 3H), 2.69 (s, 3H), 6.12 (s, 1H), 6.90-6.99 (m, 4H), 7.01-7.03 (t, 1H), 7.12-7.17 (m, 5H), 7.34-7.37 (t, 1H), 7.64-7.67 (t, 1H), 8.83 (dd, 1H).

Figure 15:
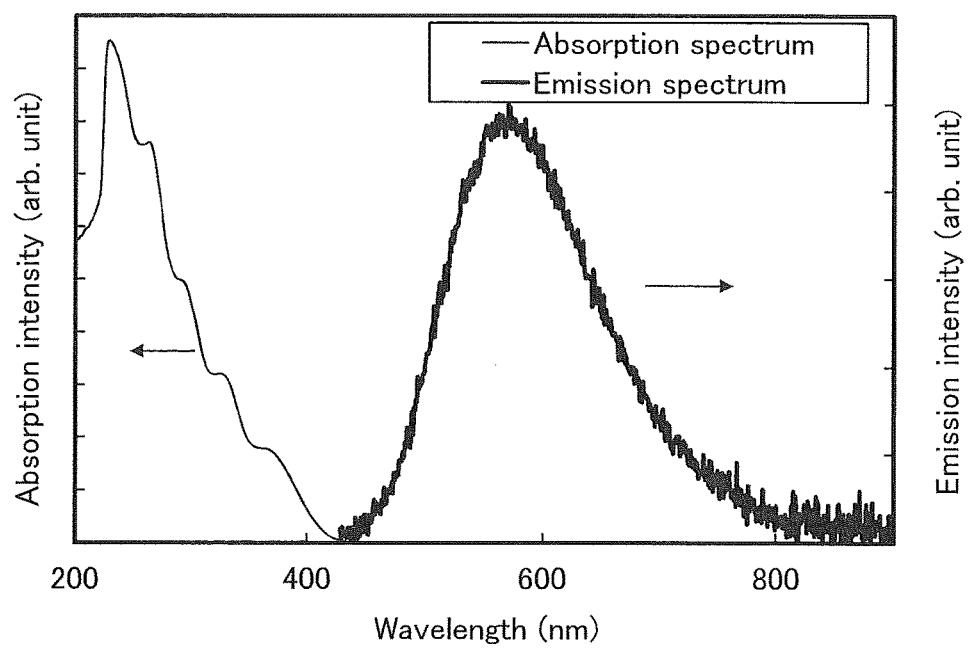
FIG. 15 shows absorption and emission spectra of [Pt(pptOppz)] at room temperature.

Next, an ultraviolet-visible absorption spectrum (hereinafter, simply referred to as absorption spectrum) and an emission spectrum of a dichloromethane solution of [Pt(pptOppz)] were measured. The measurement of the absorption spectrum was conducted at room temperature in such a manner that an ultraviolet-visible light spectrophotometer (V550 type manufactured by JASCO Corporation) was used and the dichloromethane solution (0.015 mmol/L) was put in a quartz cell. In addition, the measurement of the emission spectrum was performed at room temperature in such a manner that a fluorescence spectrophotometer (FS920 manufactured by Hamamatsu Photonics K.K.) was used and the degassed dichloromethane solution (0.015 mmol/L) was put in a quartz cell. FIG. 15 shows measurement results of the absorption spectrum and emission spectrum. The horizontal axis represents wavelength and the vertical axes represent absorption intensity and emission intensity. In FIG. 15, two solid lines are shown; a thin line represents the absorption spectrum, and a thick line represents the emission spectrum. FIG. 15 shows the absorption spectrum obtained in such a manner that the measured absorption spectrum of only dichloromethane that was in a quartz cell was subtracted from the measured absorption spectrum of the dichloromethane solution (0.015 mmol/L) that was in a quartz cell.

As shown in FIG. 15, [Pt(pptOppz)], which is the organometallic complex of one embodiment of the present invention, has an emission peak at 566 nm, and yellow emission was observed from the dichloromethane solution.

Figure 16:
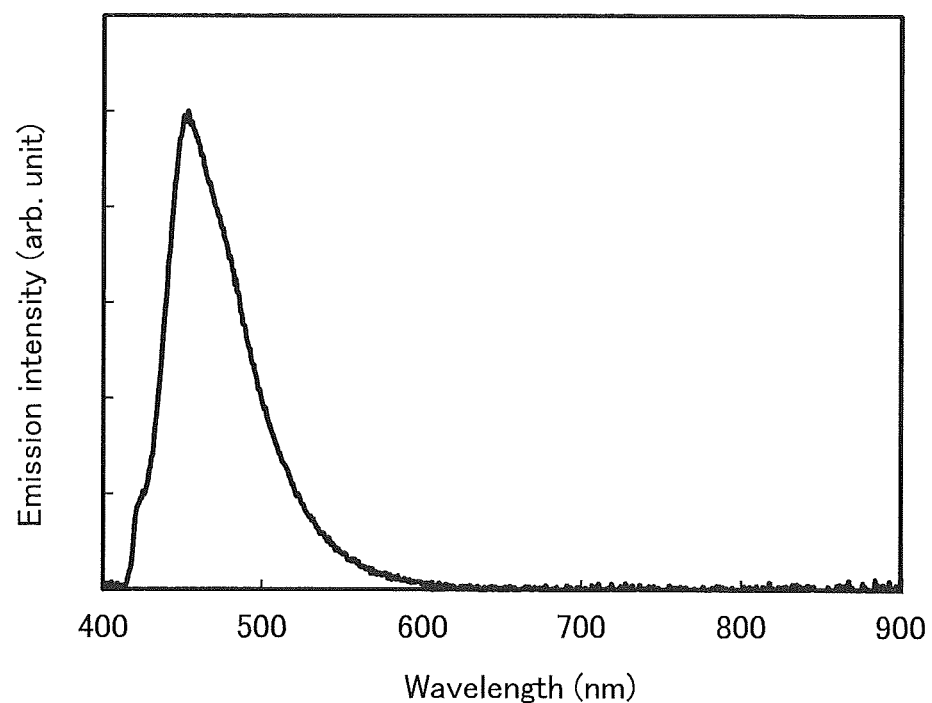
FIG. 16 shows an emission spectrum of [Pt(pptOppz)] at 77 K.

Next, an emission spectrum of [Pt(pptOppz)] at 77 K was measured. The measurement of the emission spectrum was performed in such a manner that an absolute PL quantum yield measurement system (Quantaurus-QY C11347-01 manufactured by Hamamatsu Photonics K.K.) was used and a degassed 2-methyltetrahydrofuran solution (0.079 mmol/L) was put in a quartz cell. FIG. 16 shows measurement results of the emission spectrum. The horizontal axis represents wavelength, and the vertical axis represents emission intensity.

As shown in FIG. 16, [Pt(pptOppz)], which is the organometallic complex of one embodiment of the present invention, has an emission peak at 453 nm. Blue light emission was observed from the 2-methyltetrahydrofuran solution.

The absorption at around 420 nm in the absorption spectrum of [Pt(pptOppz)] can be assigned to the triplet MLCT (metal-to-ligand charge transfer) transition, meaning that phosphorescence is possible.

Example 2

In this example, a light-emitting element using the organometallic complex of one embodiment of the present invention which is described in Embodiment is described.

Structural formulae of organic compounds used for a light-emitting element 1 are shown below.

(i)
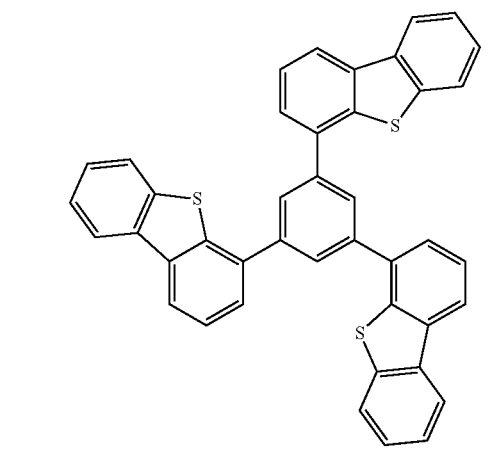
DBT3P-II (ii)
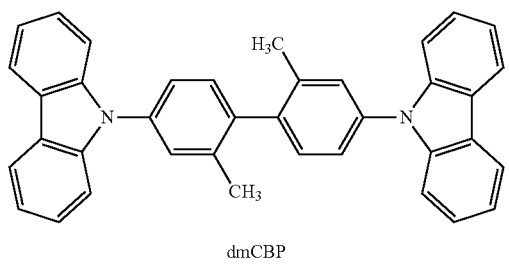
dmCBP (iii)
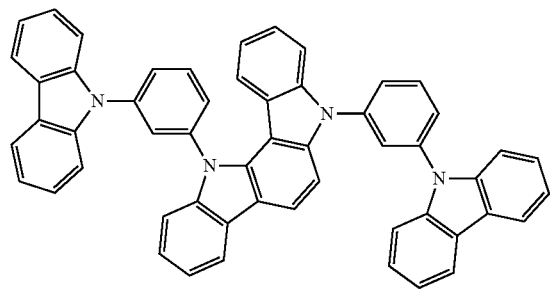
mCzP2ICz (iv)
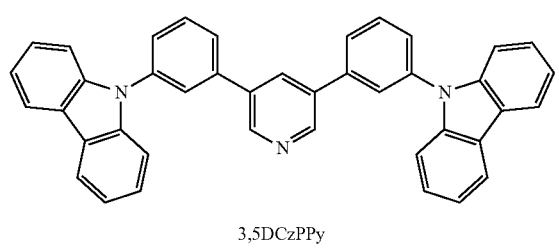
3,5DCzPPy (v)
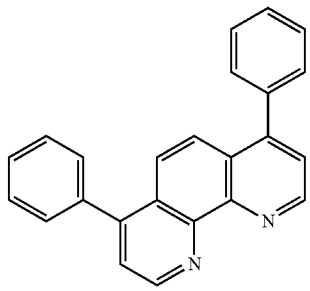
BPhen (100)
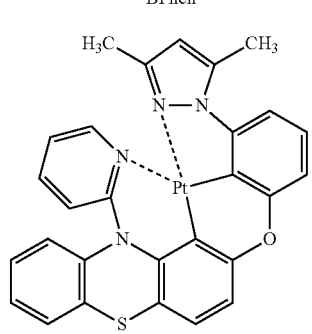

(Method for Manufacturing Light-Emitting Element 1)

First, a film of indium tin oxide containing silicon oxide (ITSO) was formed over a glass substrate by a sputtering method, so that the first electrode 101 was formed. The thickness of the first electrode 101 was set to 70 nm and the area of the electrode was set to 2 mm×2 mm.

Next, in pretreatment for forming the light-emitting element over the substrate, a surface of the substrate was washed with water and baked at 200° C. for 1 hour, and then UV ozone treatment was performed for 370 seconds.

Then, the substrate was transferred into a vacuum evaporation apparatus whose pressure was reduced to approximately $10^{-4}$ Pa, vacuum baking at 170° C. for 30 minutes was performed in a heating chamber of the vacuum evaporation apparatus, and then the substrate was cooled down for approximately 30 minutes.

Then, the substrate over which the first electrode 101 was formed was fixed to a substrate holder provided in the vacuum evaporation apparatus so that the surface on which the first electrode 101 was formed faced downward. Over the first electrode 101, 4,4',4''-(benzene-1,3,5-triyl)tri(dibenzothiophene) (abbreviation: DBT3P-II) represented by the structural formula (i) above and molybdenum(VI) oxide were deposited to a thickness of 15 nm by a co-evaporation method using resistance heating so that the weight ratio was 2:1 (=DBT3P-II: molybdenum oxide), whereby the hole-injection layer 111 was formed.

Next, 4,4'-bis(9-carbazole)-2,2'-dimethylbiphenyl (abbreviation: dmCBP) represented by the above structural formula (ii) was deposited by evaporation to a thickness of 20 nm over the hole-injection layer 111 to form the hole-transport layer 112.

Then, 5,12-bis[3-(9H-carbazol-9-yl)phenyl]-5,12-dihydro-indolo[3,2-a]carbazole (abbreviation: mCzP2ICz) represented by the above structural formula (iii), 3,5-bis[3-(9H-carbazol-9-yl)phenyl]pyridine (abbreviation: 35DCz-PPy) represented by the above structural formula (iv), and {2-[6-(3,5-dimethyl-pyrazol-1-yl-κ$N^2$)-1,2-phenylene-κ$C^1$]oxy[10-(2-pyridinyl-κN)-phenothiazine-2,1-diyl-κ$C^1$]

}platinum(II) (abbreviation: [Pt(pptOppz)]) represented by the above structural formula (100) were deposited by co-evaporation to a thickness of 30 nm so that mCzP2ICz: 35DCzPPy: [Pt(pptOppz)]=0.5:0.5:0.05 (weight ratio), and then, 35DCzPPy and [Pt(pptOppz)] were deposited by co-evaporation to a thickness of 10 nm so that 35DCzPPy: [Pt(pptOppz)]=1:0.05 (weight ratio), whereby the light-emitting layer 113 was formed.

Then, over the light-emitting layer 113, a film of 35DCz-PPy was formed to a thickness of 10 nm by evaporation, and a film of bathophenanthroline (abbreviation: BPhen) represented by the structural formula (v) was formed to a thickness of 15 nm by evaporation to form the electron-transport layer 114.

After the formation of the electron-transport layer 114, lithium fluoride (LiF) was deposited by evaporation to a thickness of 1 nm to form the electron-injection layer 115. Then, aluminum was deposited by evaporation to a thickness of 200 nm to form the second electrode 102. Through the above-described steps, the light-emitting element 1 of this example was fabricated.

The element structure of the light-emitting element 1 is shown in a table below.

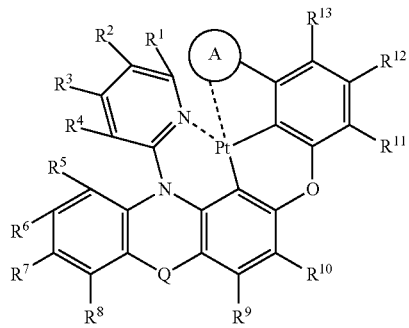

(G1)

wherein each of $R^1$ to $R^{13}$ independently represents any of hydrogen, a substituted or unsubstituted alkyl group having 1 to 6 carbon atoms, and a substituted or unsubstituted phenyl group, wherein A represents a five-membered heteroaromatic skeleton comprising two or three nitrogen atoms, and wherein Q represents a sulfur atom.

TABLE 1

| Hole-injection layer | Hole-transport layer | Light-emitting layer | | Electron-transport layer | Electron-injection layer |
|---|---|---|---|---|---|
| 15 nm | 20 nm | 30 nm | 10 nm | 10 nm | 15 nm | 1 nm |
| DBT3P-II:MoOx (2:1) | dmCBP | mCzP2ICz:35DCzPPy:[Pt(pptOppz)] (0.5:0.5:0.05) | 35DCzPPy:[Pt(pptOppz)] (1:0.05) | 35DCzPPy | BPhen | LiF |

The light-emitting element 1 was sealed using a glass substrate in a glove box containing a nitrogen atmosphere so as not to be exposed to the air (specifically, a sealing material was applied to surround the element and UV treatment and heat treatment at 80° C. for 1 hour were performed at the time of sealing). Then, the initial characteristics and reliability of the light-emitting element were measured. Note that the measurement was carried out in an atmosphere kept at 25° C.

Figure 17:
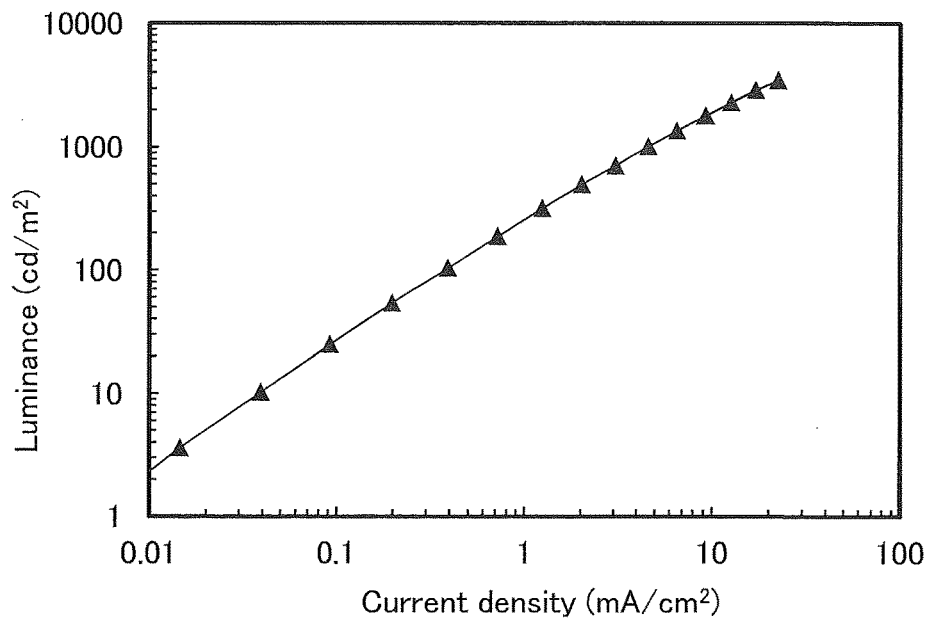
FIG. 17 shows current density-luminance characteristics of a light-emitting element 1.
Figure 18:
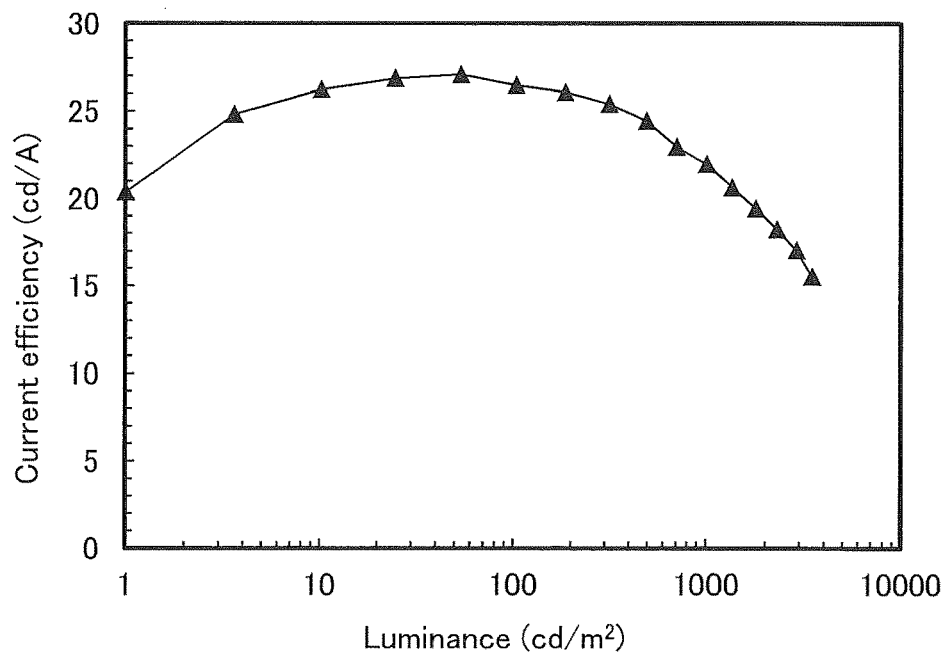
FIG. 18 shows luminance-current efficiency characteristics of a light-emitting element 1.
Figure 19:
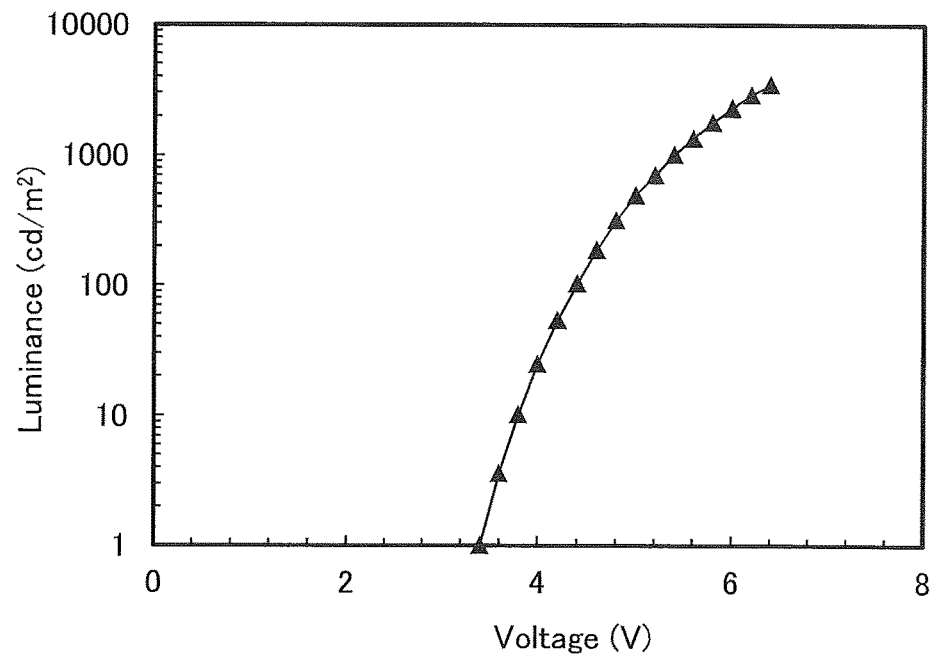
FIG. 19 shows voltage-luminance characteristics of a light-emitting element 1.
Figure 20:
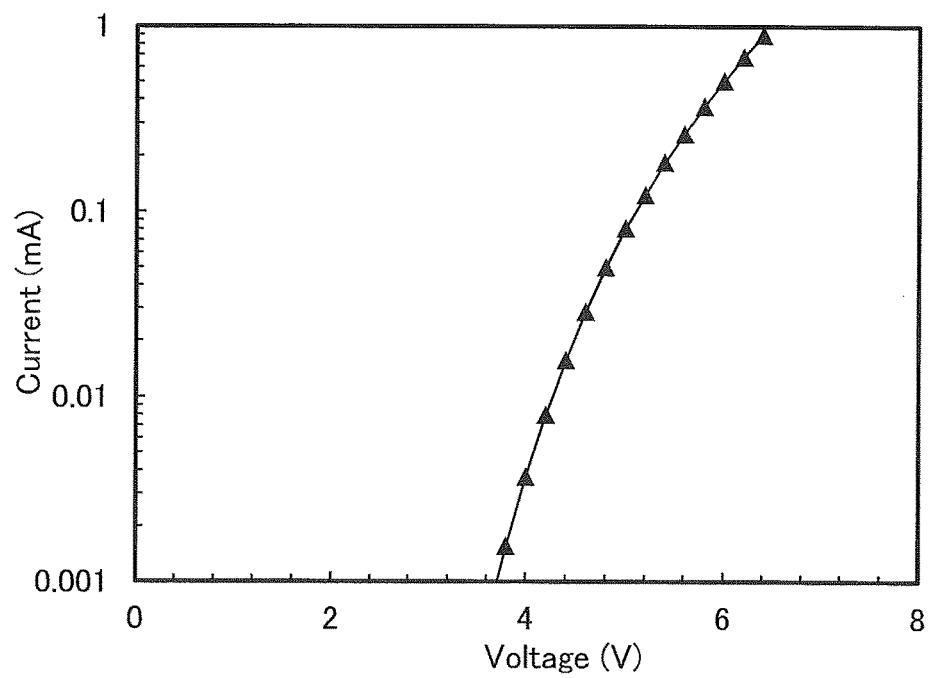
FIG. 20 shows voltage-current characteristics of a light-emitting element 1.
Figure 21:
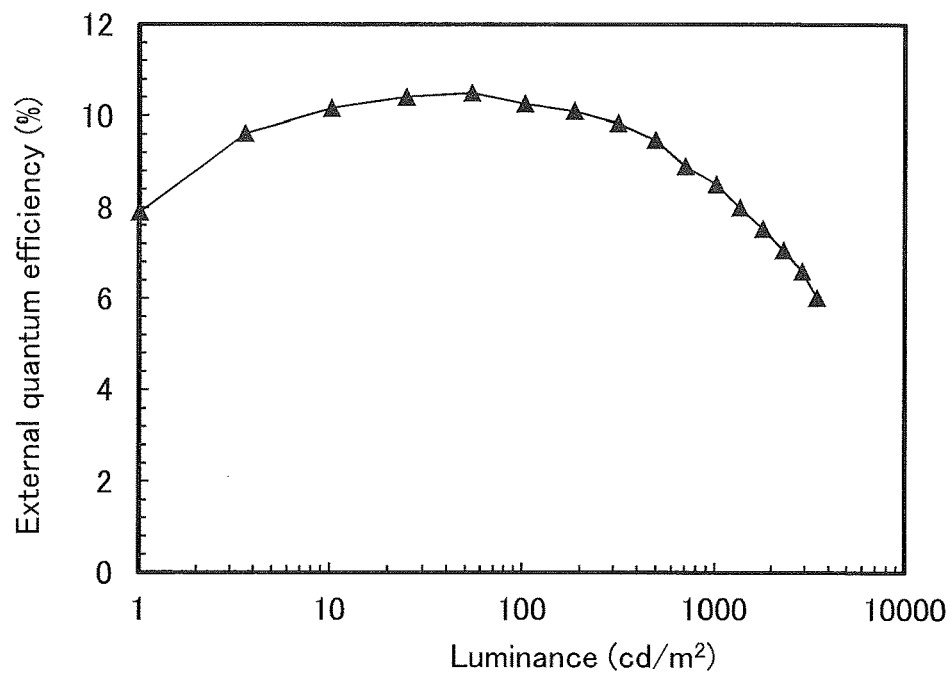
FIG. 21 shows luminance-external quantum efficiency characteristics of a light-emitting element 1.
Figure 22:
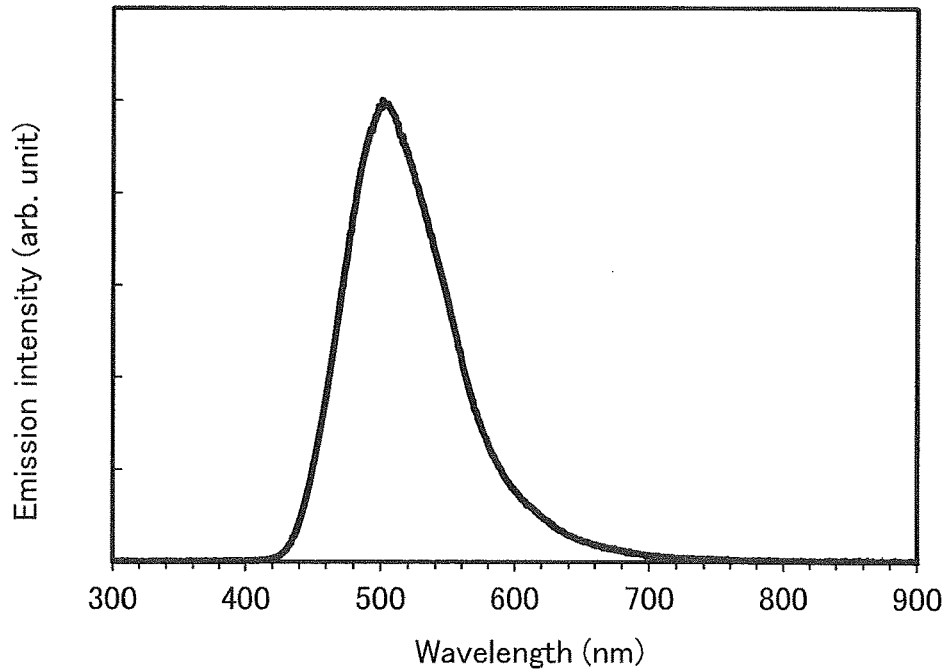
FIG. 22 shows an emission spectrum of a light-emitting element 1.

FIG. 17 shows current density-luminance characteristics of the light-emitting element 1. FIG. 18 shows luminance-current efficiency characteristics of the light-emitting element 1. FIG. 19 shows voltage-luminance characteristics of the light-emitting element 1. FIG. 20 shows voltage-current characteristics of the light-emitting element 1. FIG. 21 shows luminance-external quantum efficiency characteristics of the light-emitting element 1. FIG. 22 shows an emission spectrum of the light-emitting element 1.

FIGS. 17 to 22 reveal that the light-emitting element 1 emits green light and has high emission efficiency.

This application is based on Japanese Patent Application serial No. 2015-091000 filed with Japan Patent Office on Apr. 28, 2015, the entire contents of which are hereby incorporated by reference.

What is claimed is:
1. An organometallic complex represented by a general formula (G1),

2. An organometallic complex represented by a general formula (G4),

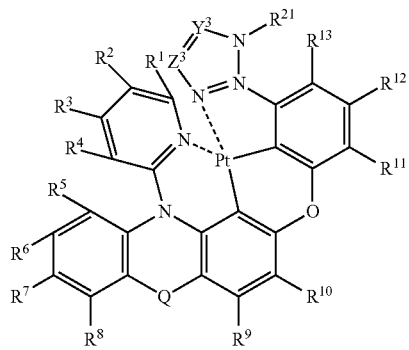

(G4)

wherein each of $R^1$ to $R^{13}$ and $R^{21}$ independently represents any of hydrogen, a substituted or unsubstituted alkyl group having 1 to 6 carbon atoms, and a substituted or unsubstituted phenyl group, wherein each of $Y^3$ and $Z^3$ independently represents a nitrogen atom or a carbon atom, wherein, when one of $Y^3$ and $Z^3$ represents a nitrogen atom, the other of $Y^3$ and $Z^3$ represents a carbon atom, wherein the carbon atom is substituted with hydrogen or with a radical other than hydrogen, and wherein Q represents a sulfur atom.

3. The organometallic complex according to claim 1 or 2, wherein $R^3$ represents a substituted or unsubstituted alkyl group.

4. The organometallic complex according to claim 3, wherein $R^3$ represents a t-butyl group.

5. A light-emitting element comprising the organometallic complex according to claim 1 or 2.

6. A light-emitting device comprising:
the light-emitting element according to claim 5; and
a transistor or a substrate.

7. An electronic device comprising:
the light-emitting device according to claim 6; and
a sensor, an operation button, a speaker, or a microphone.

8. A lighting device comprising:
the light-emitting device according to claim 6; and
a housing.

* * * * *